(12) United States Patent
Luehrs

(10) Patent No.: US 10,900,976 B2
(45) Date of Patent: Jan. 26, 2021

(54) PROCESS FOR DIAGNOSIS OF NEURODEGENERATIVE DISEASES

(71) Applicant: SeNostic GmbH, Braunschweig (DE)

(72) Inventor: Thorsten Luehrs, Braunschweig (DE)

(73) Assignee: SeNostic Health GmbH, Hannover (DE)

( * ) Notice: Subject to any disclaimer, the term of this patent is extended or adjusted under 35 U.S.C. 154(b) by 0 days.

(21) Appl. No.: 15/320,654

(22) PCT Filed: Jul. 1, 2015

(86) PCT No.: PCT/EP2015/065044
§ 371 (c)(1),
(2) Date: Dec. 20, 2016

(87) PCT Pub. No.: WO2016/001334
PCT Pub. Date: Jan. 7, 2016

(65) Prior Publication Data
US 2017/0146556 A1    May 25, 2017

(30) Foreign Application Priority Data

Jul. 1, 2014  (EP) ..................................... 14175331
Jul. 3, 2014  (EP) ..................................... 14175677

(51) Int. Cl.
| | | |
|---|---|---|
| G01N 33/68 | (2006.01) |
| G16B 20/00 | (2019.01) |
| G16B 99/00 | (2019.01) |
| G01N 1/04 | (2006.01) |
| G01N 1/28 | (2006.01) |
| G01N 21/64 | (2006.01) |

(52) U.S. Cl.
CPC ........... *G01N 33/6896* (2013.01); *G01N 1/04* (2013.01); *G01N 1/286* (2013.01); *G01N 21/6428* (2013.01); *G16B 20/00* (2019.02); *G16B 99/00* (2019.02); *G01N 2021/6439* (2013.01); *G01N 2800/2828* (2013.01); *Y02A 90/10* (2018.01)

(58) Field of Classification Search
CPC . G01N 33/6896; G01N 1/286; G01N 21/6428
See application file for complete search history.

(56) References Cited

FOREIGN PATENT DOCUMENTS

WO    2012110570 A1    8/2012
WO    2014043388 A1    3/2014

OTHER PUBLICATIONS

Eckroat et al. Amyloid-β probes: Review of structure-activity and brain-kinetics relationships. Beilstein J Org Chem. May 28, 2013;9:1012-44. doi: 10.3762/bjoc.9.116. Print 2013.*

Albert, Marilyn, S., et al., "The diagnosis of mild cognitive impairment due to Alzheimer's disease: Recommendations from the National Institute on Aging-Alzheimer's Association workgroups on diagnostic guidelines for Alzheimer's disease", Alheimers Dement., vol. 7, No. 3, (May 2011), pp. 270-279.

Barghorn, Stefan, "Purification of recombinant tau protein and preparation of Alzheimer-paired helical filaments in vitro", Methods Mol. Biol., vol. 299, (2005), pp. 35-51.

Deuschl, Guenther, "S3-Leitlinie "Demenzen": Kurzversion", German Society of Psychiatry, Psychotherapy and Neurology (DGPPN) German Society of Neurology (DGN) in cooperation with the German Alzheimer Society e.V., (Nov. 2009), 63 pages.

Eckroat, Todd, J., "Convergence of amyloid-β and tau pathologies on mitochondria in vivo", Mol Neurobiol., vol. 41, Issue 2-3, (Jun. 2014), pp. 107-114.

Eggert, K., et al., "Leitlinien: Parkinson-Syndrome—Diagnostik and Therapie", AWMF Online, (Sep. 2012), 69 pages.

Jack, Jr., Clifford, R., et al., "An Operation Approach to NIA-AA Criteria for Preclinical Alzheimer's Disease", Ann Nuerol., vol. 71, No. 6, (Jun. 2012), pp. 765-775.

Jack, Jr., Clifford, R., et al., "Introduction to Revised Criteria for the Diagnosis of Alzheimer's Disease: National Institute on Aging and the Alzheimer Association Workgroups", Alzheimers Dement., vol. 7, No. 3, (May 2011), pp. 257-262.

McKhann, Guy, et al., "Clinical diagnosis of Alzheimer's disease, Report of the NINCDS-ADRDA Work Group* under the auspices of Department of Health and Human Services Task Force on Alzheimer's Disease", Neurology, vol. 34, No. 7, (Jul. 1984), pp. 939-944.

McKhann, Guy, et al., "The diagnosis of dementia due to Alzheimer's disease: recommendations from the National Institute on Aging-Alzheimer's Association workgroups on diagnostic guidelines for Alzheimer's disease", Alzheimers Dement., vol. 7, No. 3, (May 2011), pp. 263-269.

(Continued)

*Primary Examiner* — Robert C Hayes
(74) *Attorney, Agent, or Firm* — Greer, Burns & Crain, Ltd.; Steven P. Fallon

(57) ABSTRACT

The invention provides an analytical process for analysing the presence of at least one aggregated conformation prion protein in a sample of body fluid or a sample of tissue and uses the dependency of the amplification of the aggregated conformation on the shear-force intensity applied to the native conformation prion protein, which is also dependent on the specific seed present in the admixture with native conformation prion protein, for specifically analysing for the presence of an aggregated conformation prion protein in the sample. The process of the invention contains the step of determining the content of aggregated conformation prion protein generated in admixture with the sample to be analysed using one shear-force intensity, preferably using least at two different shear-force intensities and the step of comparing data on these contents of generated prion protein having an aggregated conformation with data on the content of aggregated prion protein that is pre-determined, each at the same shear-force intensity for a mixture of the same native conformation prion protein with a reference sample as a seed.

9 Claims, 11 Drawing Sheets

(56) References Cited

OTHER PUBLICATIONS

Figure 1:
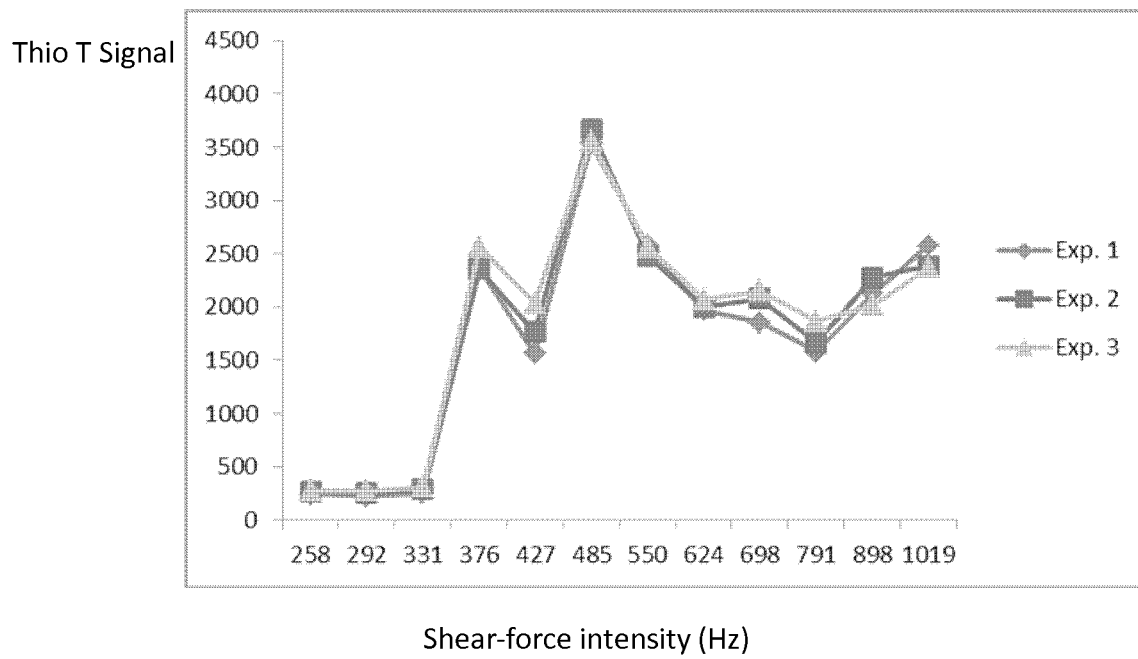
Figure 2:
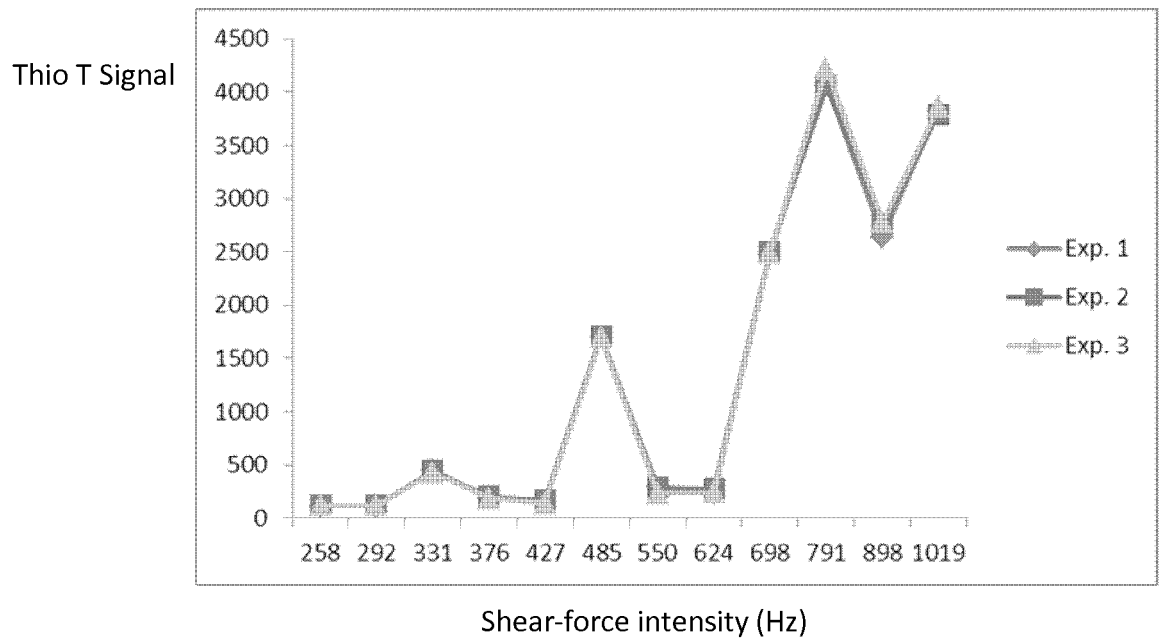
Figure 3:
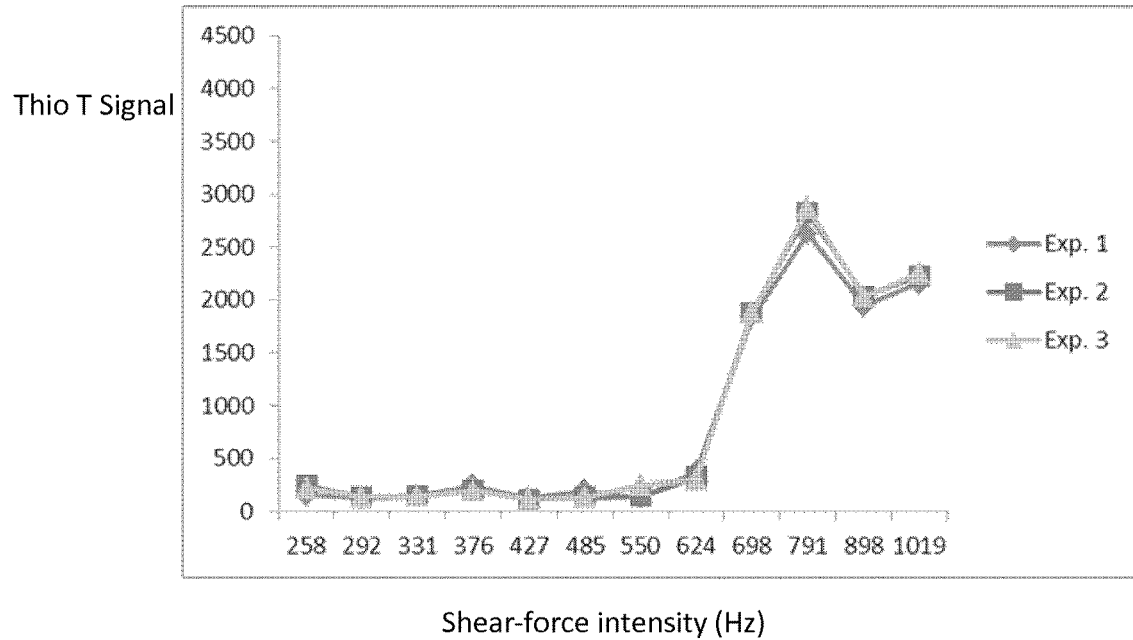
Figure 4:
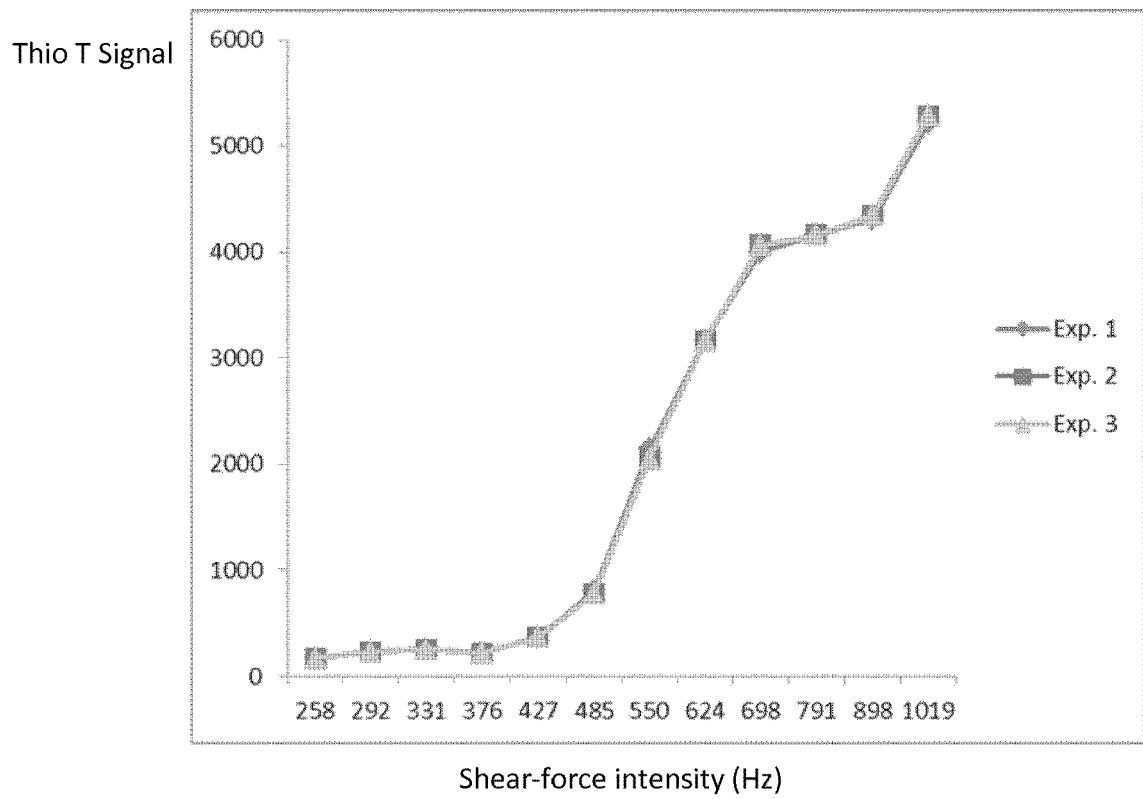

Salvadores, N., "Detection of misfolded Aβ oligomers for sensitive biochemical diagnosis of Alzheimer's disease", Cell Rep., No. 7, vol. 1, Apr. 10, 2014, pp. 261-268.

Sperling, Reisa, A., "Toward defining the preclinical stages of Alzheimer's disease: Recommendations from the National Institute on Aging-Alzheimer's Association workgroups on diagnostic guidelines for Alzheimer's disease", Alzheimers Dement., vol. 7, No. 3, (May 2011), pp. 280-292.

Surewicz, Witold, K., "OR-01: The challenge of structural understanding of prion protein conversion and prion propagation", Oral Presentations, Prion 6: Supplement 1, 2-22; (Apr./May/Jun. 2012), 21 pages.

Borinski, Wolfgang, "International Search Report and Written Opinion", Patent Cooperation Treaty Application No. PCT/EP2015/065044, European Patent Office as Search Authority, dated Sep. 14, 2015, 9 pages.

\* cited by examiner

Shear-force intensity (Hz)

Shear-force intensity (Hz)

Shear-force intensity (Hz)

Shear-force intensity (Hz)

Shear-force intensity (Hz)

Shear-force intensity (Hz)

3 mm

PROCESS FOR DIAGNOSIS OF NEURODEGENERATIVE DISEASES

The present invention relates to an analytical process for use in the diagnosis and classification of neurodegenerative diseases, especially neurodegenerative diseases associated with protein misfolding or protein aggregation, and to a device for use in the process. Herein, neurodegenerative diseases associated with protein misfolding are also collectively referred to as prion-aggregate related diseases, including e.g. amyloidoses, and proteopathies that include synuclein aggregation diseases (synucleopathies), tau aggregation diseases (tauopathies) and Alzheimer beta (Aβ) peptide aggregation diseases. Preferred diseases are neurodegenerative disorders and dementias, e.g. Alzheimer's disease, frontotemporal lobular dementia, Parkinson disease, Dementia with Lewy Bodies, Parkinson's Disease with Dementia, Multiple System Atrophy, amyotrophic lateral sclerosis, motor neuron disease and Huntington disease. These diseases are accompanied by occurrence of aggregated conformation prion protein which presents a suitable pathological analyte having specificity for such a disease. The aggregated conformation prion protein can be transmissible and is able to induce native conformation prion protein to change its conformation to the aggregated conformation associated with disease pathology. Further, the invention relates to a device for use in the process.

STATE OF THE ART

Salvadores et al., Cell Reports 261-268 (2014) describe the detection of aggregated Amyloid-β (Aβ) protein for diagnosis of Alzheimer's disease by incubating in a temperature-controlled shaker a cerebrospinal fluid (CSF) sample with aggregate-free Aβ peptide and Thioflavin T. Amyloid formation was determined by intermediate fluorometry using a plate spectrofluorometer for Thioflavin T binding to amyloid fibrils.

WO 2012/110570 A1 describes a process for the amplification of aggregated conformation prion protein from native conformation prion protein in admixture with aggregated conformation prion protein using shear-force control. Optionally, aliquots of an admixture are subjected to different intensities of controlled shear-force. The disclosure of WO 2012/110570 is contained herein by reference.

Eckroat et al., Beilstein J. Org. Chem. 2013, 1012-1044 describe dye probes for Amyloid-ß. McKhann et al, Neurology. 34(7), 939-44 (1984), Jack Jr et al, Alzheimers Dement. 2011 7(3), 257-262, McKhann et al., Alzheimers Dement. 7(3): 263-269 (2011), Albert et al., Alzheimers Dement. 7(3): 270-279 (2011), Sperling et al., Alzheimers Dement. 7(3): 280-292 (2011) and Jack Jr et al., Ann. Neurol. 71(6): 765-774 (2012) as well as Eggert K, et al. "Leitlinien: Parkinson-Syndrome—Diagnostik und Therapie", AWMF-Register Nr. 030/010, Stand 09/2012, and Deutsche Gesellschaft für Psychiatrie, Psychotherapie und Nervenheilkunde (DGPPN), "S3 Praxisleitlinie: Diagnose- und Behandlungsleitlinie 'Demenz'" describe diagnostic criteria for classifying neurodegenerative diseases. Barghorn et al., Methods in Molecular Biology, Vol 299, 2005: Amyloid Proteins: Methods and Protocols, pages 35-51, "Purification of recombinant tau protein and preparation of Alzheimer-paired helical filaments in vitro" describe isoforms of human tau protein.

OBJECT OF THE INVENTION

It is an object of the invention to provide an analytical process that allows to detect an analyte specific for a prion-aggregate related disease using a biopsied sample obtained from a mammal, especially a human or an experimental mammal, e.g. a mouse or rat. A preferred object is an analytical process that allows for a differential diagnosis, more preferably prior to onset or early at onset of clinical symptoms of the disease.

DESCRIPTION OF THE INVENTION

The invention attains the object, especially the differential diagnosis of a prion-aggregate related disease by the features of the claims, especially by an analytical process for analysing for the presence of at least one aggregated conformation prion protein in a sample of body fluid or in a sample of tissue originating from a mammal, preferably biopsied from a human, especially of a preclinical patient or a patient suspected of having a neurodegenerative disease, e.g. a patient suspected of having a neurodegenerative disease on the basis of phenomenological diagnostic criteria as described in the state of art. The sample can comprise or consist of blood, preferably blood serum, urine and/or cerebrospinal fluid (CSF), or any other solid tissue, e.g. a tissue sample that preferably contains a nerve section, for example a skin biopsy. The mammal preferably is a human, a farm animal used for food production, e.g. a bovine, deer, elk, swine, sheep, goat, fowl, or an experimental animal, e.g. a mouse, rat or non-human primate. The animal can also be a wild mammal, for example wild goat, deer or elk. Herein, the generation of aggregated conformation prion protein from an admixture comprising native conformation prion protein and a sample containing aggregated conformation prion protein with application of shear-force is also referred to as amplification.

For the purposes of the invention, neurodegenerative diseases also include posttraumatic stress disorder (PTSD, e.g. ICD10 F43.1) that may develop in persons after being exposed to one or more traumatic events, e.g. sexual assault, fighting in a war, sustaining serious injury or threat of death with the experience of intense fear, horror, or powerlessness, as well as restless leg syndrome, (RLS, e.g. G25.8), also known as Willis-Ekbom disease (WED) of Wittmaack-Ekbom syndrome, a neurological disorder characterized by an irresistible urge to move one's body to stop uncomfortable or odd sensations, e.g. affecting the legs, arms, torso, head or even phantom limbs, the movement providing temporary relief.

During the preparation of the invention it has been found that aggregated conformation prion protein induces the change in conformation of native prion protein in dependence on the shear-force intensity applied to a mixture of these, and that the change in conformation can in addition depend on the specific aggregated conformation prion protein added to the native conformation prion protein. As used herein, native prion protein relates to the non-aggregated conformation protein that undergoes a change in conformation in the presence of aggregated conformation prion protein (seed) to aggregated conformation prion protein. Accordingly, native prion protein can also be referred to as non-aggregated prion protein. In greater detail, it has been found that depending on the source, the aggregated conformation prion protein when subjected to specific shear-force in admixture with native conformation prion protein can yield amplification of an aggregated conformation only for specific shear-force intensities, whereas little or no amplification of the aggregated conformation occurs at different shear-force intensities, e.g. different shear-force intensities yield a different pattern of aggregated conformation generated from the original native conformation prion protein. The aggregated conformation prion protein is also termed proteopathic seed, or seed. For example, the seed and the native conformation prion protein in the mixture subjected to different shear force intensities can have the same amino acid sequence, resulting in the amplification of aggregated conformation prion protein from the native conformation prion protein only at specific shear-force intensities. Accordingly, the invention uses the dependency of the amplification of the aggregated conformation on the shear-force intensity applied to the native conformation prion protein, which is also dependent on the specific seed present in the admixture with native conformation prion protein, for specifically analysing for the presence of an aggregated conformation prion protein in the sample. Accordingly, the process of the invention contains the step of determining the content of aggregated conformation prion protein generated in admixture with the sample to be analysed using one shear-force intensity, preferably using least at two different shear-force intensities and the step of comparing data on these contents of generated prion protein having an aggregated conformation with data on the content of aggregated prion protein that is pre-determined, each at the same shear-force intensity for a mixture of the same native conformation prion protein with a reference sample as a seed. The at least two different shear-force intensities can e.g. be at least 3, preferably at least 4 to at least 12, e.g. up to 24 or up to 36 different shear-force intensities. Generally preferred, the shear-force intensity of the process is pre-determined and identical for the sample and for use in the generation of pre-determined data on the content of aggregated conformation prion protein, especially generated from an admixture of native conformation prion protein and a reference sample. The shear-force intensity can generally be pre-determined in respect of duration of shear-force application for each cycle, duration of resting phase for each cycle, and number of repetition of cycles.

Preferably, the pre-determined data on the content of aggregated conformation prion protein generated is determined separately for each of at least two mixtures of the same native conformation prion protein with a seed, each mixture containing a different reference sample as a seed, which is e.g. obtained from a different reference patient having a known diagnosis for a neurodegenerative disease, for example determined by conventional diagnostic schemes. Convential diagnostic schemes are diagnostic guidelines for dementia and Parkinson syndromes, e.g. the classification according to McKhann et al, "Clinical diagnosis of Alzheimer's diesease: report of the NINCDS-ADRDA Work Group under the auspices of Department of Health and Human Services Task Force on Alzheimer's Disease, Neurology. 34(7), 939-44 (1984), preferably according to the overview by Jack Jr et al., "Introduction to revised criteria for the diagnosis of Alzheimer's disease: National Institute on aging and the Alzheimer association workgroups, Alzheimers Dement. 2011 7(3), 257-262, in respect of AD more preferred according to McKhann et al., "The diagnosis of dementia due to Alzheimer's disease: Recommendations from the National Institute on Aging—Alzheimer's Association workgroups on diagnostic guidelines for Alzheimer's disease", Alzheimers Dement. 7(3): 263-269 (2011), in respect of mild cognitive impairment (MCI) due to AD preferably according to Albert et al., "The diagnosis of mild cognitive impairment due to Alzheimer's disease: Recommendations from the National Institute on Aging—Alzheimer's Association workgroups on diagnostic guidelines for Alzheimer's disease", Alzheimers Dement. 7(3): 270-279 (2011), in respect of preclinical AD preferably according to Sperling et al., "Towards defining the preclinical stages of Alzheimer's disease: Recommendations from the National Institute on Aging—Alzheimer's Association workgroups on diagnostic guidelines for Alzheimer's disease", Alzheimers Dement. 7(3): 280-292 (2011) and/or according to Jack Jr et al., "An operational approach to NIA-AA criteria for preclinical Alzheimer's disease", Ann. Neurol. 71(6): 765-774 (2012), and/or according to Eggert K, et al. "Leitlinien: Parkinson-Syndrome—Diagnostik und Therapie", AWMF-Register Nr. 030/010, Stand 09/2012, and/or according to Deutsche Gesellschaft für Psychiatrie, Psychotherapie und Nervenheilkunde (DGPPN), "S3 Praxisleitlinie: Diagnose—und Behandlungsleitlinie 'Demenz'". Preferably, data on these pre-determined amounts which are specific for at least one shear-force intensity, preferably for at least two different shear-force intensities and specific for a reference sample from a specific source are contained and provided in a computer-based databank, and the comparison is carried out by a computer.

The specific reference sample can for example be selected from a sample of body fluid or tissue of a patient, alive or deceased, with a diagnosis for a specific neurodegenerative disease or a subtype thereof. Preferably, the databank contains the diagnosis for a specific neurodegenerative disease and/or a subtype thereof in association with pre-determined data on amounts of aggregated conformation prion protein, each generated at one of at least two, e.g. 3, 4, 12, 24, or 36 different shear-force intensities for each reference sample. Generally, the sample to be analysed and the reference sample can be admixed with the same native conformation prion protein and subjected to the same shear-force intensities.

The shear-force dependent amplification of the aggregated conformation is made by subjecting the mixture comprising or consisting of the sample of body fluid and at least one native conformation prion protein to at least two different shear-force intensities. The shear-force intensities are controlled to have a uniform intensity having an intensity range of maximally 20% or maximally 15% or 12%, e.g. maximally 10%, preferably maximally 5%, more preferably maximally 2% or maximally 1% of one shear-force value.

In a first preferred embodiment, the mixture comprising the mammalian sample, e.g. of body fluid and/or tissue, and at least one native conformation prion protein is subjected to at least two different shear-force intensities by dividing the mixture into aliquots (portions of the mixture) and subjecting each of the aliquots to one of the at least two shear-force intensities. Preferably, the aliquots are subjected to one of the shear-force intensities each in parallel, preferably using identical devices or identical sections of devices for generating the shear-force intensities.

In a second preferred embodiment, the mixture or an aliquot thereof is subjected to at least two different shear-force intensities sequentially, e.g. subjected firstly to one of the shear-force intensities and later to another of the shear-force intensities. In this embodiment, the determination of the content of aggregated conformation is made during and/or subsequent to application of one shear-force intensity and/or subsequent to application of each shear-force intensity.

The first and second embodiments can be combined, e.g. to a process in which at least two aliquots of the mixture are each subjected sequentially to different shear-force intensities, e.g. the mixture or at least two aliquots thereof are subjected to one first shear-force intensity and subsequently to a least one second shear-force intensity, each shear-force intensity differing from the other.

In the process, native conformation prion protein is contacted with aggregated conformation prion protein (seed) in a liquid composition and subjected to at least one cycle or to a number of cycles of application of shear-force for fragmenting aggregates of prion protein, wherein the shear-force applied is precisely controlled, e.g. to a range of maximally 20% or maximally 15% or 12%, e.g. maximally 10%, preferably maximally 5%, more preferably maximally 2% or maximally 1% of one shear-force value, more preferably to 0.5% intensity range around one shear-force intensity value, wherein optionally each cycle contains at least one second phase of incubation without agitation and/or at least one phase of agitation at one shear-force intensity value, which is different from the first shear-force intensity value, which is e.g. zero or 1 to 50%, preferably zero of the first shear-force intensity value. The second phase of incubation, also referred to as a resting phase, is included for allowing the aggregation of native conformation prion protein with aggregated conformation prion protein. Optionally, the product obtained by the process of the invention can be used as aggregated conformation protein, e.g. as seed for pre-determination of the content of aggregated state prion protein. For the pre-determination the seed in admixture with native conformation prion protein is subjected to at least one cycle or to a number of cycles of application of shear-force for fragmenting aggregates of prion protein as described herein.

Native conformation prion protein can e.g. be produced by expression in a cultivated cell which is genetically manipulated to contain an expression cassette encoding the prion protein and isolating the prion protein from the cultivated cell and/or from the medium of a culture of the cells. Cells for expression of prion protein can be bacteria, preferably *E. coli*, yeast, fungi, and mammalian cells, e.g. human cells or hamster CHO cells. Native conformation prion protein can also be produced from mammalian tissue.

The shear-force intensities can be generated as cycles or repetitions of a fragmentation phase with a subsequent resting phase without shear-force being applied, e.g. each fragmentation phase consisting of 1 s to 240 s, preferably 30 s to 120 s and each subsequent resting phase consisting of 10 s to 1080 s, preferably 60 s to 540 s. The cycles or repetitions of the fragmentation phase and the subsequent resting phase can e.g. be from 1 to 500 cycles, e.g. 5 to 500, preferably 60 to 280 cycles, e.g. 100 to 140 cycles. In each cycle, the shear-force is controlled to be within an intensity range of maximally 10%, preferably maximally 2%, more preferrably maximally 1%, e.g. within 0.5% or within 0.1% of one shear-force intensity.

The shear-force having an intensity that is controlled to have a uniform intensity having an intensity range of maximally 20% of one shear-force value can be generated by a shear-force generator comprising or consisting of a rotary element arranged in a sample vessel having a lid, wherein the rotary element is run on bearings which are coaxially arranged within the sample vessel, and wherein the rotary element comprises a first coupling element of a coupling, e.g. comprising or consisting of a permanent magnet, which preferably is at least bipolar or quadrupolar. The first coupling element is arrangeable for coupling with the second coupling element of the coupling, e.g. a driving coil arrangement which can be arranged surrounding the first coupling element. Preferably, the outer surface of the rotary element is parallel to the inner wall surface of the vessel, e.g. the rotary element and a coaxial section of the inner wall surface of the vessel are spaced and cylindrical or conical. Preferably, the bearing of the rotary element comprises or consists of an axle, one end of which is arranged contacting a bottom section of the inner vessel surface and the other end of which runs in a bearing attached next to the rim of the vessel, e.g. by frictional connection and/or by positive fit.

Alternatively, the shear-force can be generated by a shear-force generator having a rotary element coaxially arranged in a radially spaced tube section, the radial spacing of the rotary element and the tube and the axial section in which both the rotary element and the tube extend defining a space, e.g. of ring-shaped cross-section, in which space upon rotation of the rotary element shear-force is generated. Preferably, the rotary element along its longitudinal and rotary axis has a constant outer diameter and is arranged at a constant spacing from the encircling tube section. The rotary element can take any outer form, preferably of axial symmetry, e.g. a flat shape or a rectangular cross-section and preferably has a cylindrical outer surface. Preferably, the tube in its section encircling the rotary element has a cylindrical inner cross-section. Along the common longitudinal axis, the tube preferably at one end of the section encircling the rotary element extends over the rotary element, such that the rotary element ends at a distance from the end of the tube, allowing a suction action at rotation of the rotary element, and at the opposite end of the section encircling the rotary element, the rotary element extends over at least one exit opening in the walls of the tube, allowing liquid to exit. Preferably, the at least one exit opening in the walls of the tube has a cross-section of at least the cross-section of the area between the tube and the rotary element, more preferably, the exit opening has a cross-section of or greater than the inner cross-section of the tube, and most preferably, the exit opening is the cross-section of the tube.

This shear-force generator is arranged within a vessel containing a liquid preparation of prion protein, as rotation of the rotary element in addition to exerting a shear-force of one pre-set intensity, which is controlled to a narrow range, generates a suction at the end which is protruded by the encircling tube section such that all volume elements of the liquid are moved through the space between the rotary element and the encircling tube section, where the volume elements are consecutively subjected to the shear force.

The rotary element is arranged in a bearing, which is preferably coaxial to the tube and to the rotary element, e.g. the bearing can be arranged in a tube section adjacent the at least one exit opening and opposite the section encircling the rotary element. Preferably, the bearing comprises or consists of a low-friction polymer tube, e.g. poly tetrafluoro ethylene (PTFE), optionally having at least 2 or at least 4 longitudinal convex or concave folds, arranged in a tube section adjacent the exit openings, between the rotary element and the tube encircling it. The low-friction polymer tube of the bearing preferably is arranged between one circumferential shoulder extending from the rotary element and one circumferential shoulder protruding from the inner surface of the tube, e.g. one shoulder at one of the opposite ends of the bearing.

The shear force is controlled and set to a specific value by controlling the rotation rate of the rotary element, preferably by controlling the drive motor coupled to the rotary element.

Preferably, the shear force generator is controlled to one pre-set shear-force intensity corresponding to a rotation rate between 10 and 10.000 Hz, preferably between 50 and 5000 or up to 2000 or 1000 Hz, precisely controlled to a range of maximally 1% of the rotation rate set, more preferably to a rotation rate with range of maximally +/−2 Hz, more preferably of maximally +/−1 Hz, with an outer diameter of the rotary element of 1.95-2.05 mm arranged in a tube section with an inner diameter of 1.55-2.75 mm, wherein the rotary element is a cylinder, optionally having a square flat end section.

In the alternative, the shear-force having a controlled shear-force intensity can be generated by a shear-force generator which is a sonicator, also referred to as an ultrasound emitter, which has a vessel for receiving the liquid preparation containing the mixture to be subjected to shear-force, the vessel having an inner volume which extends for a volume element only that is arranged in the distance from the sonicator surface (or sonotrode surface) and is parallel to the surface section only, in which at least 75% to 90%, preferably at least 95%, more preferably at least 99% of the maximum amplitude is positioned. This volume element is e.g. arranged within the distance of 0.5 mm to 50 mm from the surface of the sonicator and extends in parallel to the center of the surface fraction between vibration nodes of the sonicator surface, e.g. for maximally 10%, preferably for maximally 2% or 1% of the area between vibration nodes. The position of the volume element can e.g. be pre-determined by calculation of the surface fraction of the sonotrode surface and the distance from the sonotrode surface in which maximum amplitude, and hence maximum shear-force is generated. Due to the specific arrangement of the volume element in the maximum vibration intensity, the liquid composition therein is subjected to a shear-force having an intensity of the limited intensity range. For an efficient transfer of vibrations from the sonotrode surface to the volume element, the vessel preferably consists of a material that is permissive to ultrasound, e.g. of polypropylene, poly tetrafluoro ethylene (PTFE) or other types of teflon, and a transfer liquid, e.g. water, is arranged between the vessel and the sonotrode surface. Preferably, the sonotrode forms one wall of a transfer liquid bath, e.g. a side wall and preferably the bottom wall, and the height of the transfer liquid in perpendicular to the sonotrode surface is set to one wavelength of the ultrasound, e.g. at the resonance frequency of the sonotrode, or to an integral multiple of the wave-length of the ultrasound, e.g. at the resonance frequency of the sonotrode. The transfer liquid bath can be adapted or designed to pre-set the height of the transfer liquid, the height being determined in perpendicular to the sonotrode surface.

Preferably, the devices are arranged in an array of two or more devices, e.g. 7, 8, 12, 14 or 21 devices, arranged with their longitudinal axes vertically in a temperature-controlled housing. All devices of the array can be connected to and controlled by one computer, which is provided for controlling the rotation rate of each rotary element individually. This array of devices is advantageous for treating aliquots of one liquid composition of prion protein in parallel, i.e. without variation of the composition or state of the liquid composition, as e.g. could occur in subsequent treatment processes during storage of aliquots and day-to-day variations of treatment conditions. Using the array of devices, the process of the invention comprises the treatment of aliquots of one liquid composition comprising the mixture of native conformation prion protein and seed in separate single devices concurrently, preferably with differing shear-forces each, which are generated by different rates of rotation applied to the rotary elements.

Generally, the device contains a control unit which is set for controlling the shear-force generator to at least one pre-set shear force intensity to a range limited to a maximum of 10% of one shear-force value, e.g. of the maximum shear-force, e.g. by setting or controlling a drive contained in or coupled to the shear-force generator to a maximum range of 10% of one frequency, e.g. to a maximum of 10%, preferably of 1% or 0.1% of one frequency, e.g. of a pre-determined frequency or of the resonance frequency of the shear-force generator. The control unit can be a computer separate from the computer controlling the shear-force generators or can be contained in the same computer. Preferably, both the control unit and the computer controlling the shear-force generators are set up to store the shear-force intensities for each shear-force generator and are preferably set up to additionally store measuring results representing the content of aggregated conformation prion protein, each in relation to the shear-force intensities. The measuring results representing the content of aggregated conformation prion protein can be optical measurement results from protein size separation, e.g. by chromatographic methods like size exclusion chromatography, or electrophoresis, e.g. SDS-PAGE, optionally from Western blots for the admixture for optical density of specific bands, or optical measurement results for luminescence, for absorbance or for light scatter generated by an optical detector arranged to receive irradiation from the inner volume of the container for the admixture.

The device comprises or has access to a databank containing data on amounts of aggregated conformation prion protein, which data are pre-determined for one specific shear-force intensity, preferably for at least two different shear-force intensities for a reference sample from a specific source of known diagnosis. The device, e.g. its computer, is set up for comparing the data provided in the computer-based databank to data representing amounts of aggregated conformation prion protein generated from an admixture of sample and native conformation prion protein, wherein the comparison of amounts of aggregated conformation prion protein is made for the same shear-force intensity.

Generally preferred, all admixtures containing native conformation prion protein and aggregated conformation prion protein, e.g. reference sample or sample to be analysed, are in the same aqueous buffer, e.g. the same concentration of the same salts at the same pH value and at the same temperature for all measurements.

The native conformation prion protein can e.g. be produced by expression in a microorganism or in a cultivated cell, or be chemically synthesized. Preferably, the native conformation prion protein is provided in aqueous solution.

Following or during subjecting the mixture or aliquots thereof, the content or increase of aggregated conformation prion protein is detected. Generally, it is preferred to detect the amount of aggregated conformation prion protein using an optical detector, which can be separate from the shear-force generator so that the container containing the aggregated conformation prion protein is transferred from the shear-force generator to the detector, which can e.g. be a plate reader. In the alternative, the optical detector can be arranged at the container while the container is arranged at the shear-force generator, e.g. for measurement during resting phases of application of shear-force intensities. In addition or in the alternative, the aggregated state prion protein obtained by the process can be detected, optionally following contacting with proteinase, by size separation, e.g. chromatographically or electrophoretically, optionally with antibody detection, e.g. in a Western blot, and/or by structure sensitive spectroscopy, e.g. by infrared spectroscopy (IR), preferably Fourrier-transformed IR (FT-IR), by NMR, especially $^{13}$C-NMR, and/or fluorescence spectroscopy, preferably after addition of a fluorescence dye being specific for aggregated conformation prion protein. These detection steps have the advantage of providing structure-related information on the aggregated state prion protein generated, especially following contacting the aggregated conformation prion protein with proteinase due to differences in proteinase resistance of aggregated conformation prion protein.

Preferably, detection is by measuring the change of fluorescence of a fluorescent dye added to the mixture, the dye being specific for aggregated conformation prion protein. Exemplary dyes are those mentioned in Eckroat et al., quoted above, e.g. Thioflavin T, Thioflavin S, Congo Red, thiophene-based amyloid ligands like luminescent conjugated polythiophenes (LCP), polythiophene acetic acid (PTAA) and luminescent conjugated oligothiophenes (LCO), Pittsburgh compound B, Aminonaphthalene 2-Cyanoacrylate (ANCA) probes, pegylated phenylbenzoxazole derivatives, Pinacyanol, Chrysamine G, and dyes containing at least on of the following scaffolds: Chalcone, Flavone, Aurone, Stilbene, Diphenyl-1,2,4-oxadiazole, Diphenyl-1,3,4-oxadiazole, Benzothiazole, Benzooxazole, Benzofuran, Imidazopyridine, Benzimidazole, Quinoline, Naphthalene.

In the alternative, the native conformation prion protein can be labelled with a fluorescent dye, e.g. by binding of a fluorescent dye to the native conformation prion protein directly or by an intermediate spacer, e.g. fluorophore derivatives that contain reactive chemical groups such as isothiocyanates (reactive to primary amines, e.g. Lysines), succinylimide esters (reactive towards amino groups to form amido bonds, e.g. N-terminal amino acids), maleimide (reactive to free sulfhydryl groups, e.g. cysteine). Such fluorophore derivatives include cyanines, flurescein, rhodamine, Alexa Fluors, Dylight fluors, ATTO-Tec Dyes, BODIPY Dyes, SETA Dyes, SeTau Dyes, DYOMICS Dyes.

Optionally, the process can comprise the additional step of contacting the admixture following application of shear-force intensity with at least one compound selected from Thioflavin T, Thioflavin S, Congo Red, thiophene-based amyloid ligands like luminescent conjugated polythiophenes (LCP), polythiophene acetic acid (PTAA) and luminescent conjugated oligothiophenes (LCO), which compounds can be conformation-specific for aggregated conformation prion protein. This optional additional step allows for distinguishing aggregated conformations of prion protein by measuring their fluorescence. As some of these compounds can interfere with the change in conformation from native to aggregated conformation, at least one of them is contacted with the admixture only subsequent to application of the shear-force intensity. The addition of at least one of these compounds and the resultant fluorescence measurement is stored in the databank.

In the process comprising detection of aggregated conformation prion protein, the device according to the invention can be used as a detector for the presence of seed in a sample. The device comprises at least one container for receiving the admixture comprising the sample, the container being coupled to or comprising a shear-force generator, preferably at least two containers with one shear-force generator for each container. For detection, each container is provided with an irradiation source and an optical detector, preferably a fluorescence detector, both directed at the container provided for receiving the mixture of seed and native conformation prion protein. For example, the device comprises at least one, preferably at least two containers for receiving a mixture of seed and native conformation prion protein, each container provided with a shear-force generator that is controlled to generate at least one, optionally sequentially at least two different shear-forces, and is provided with an optical detector arranged for receiving light emitted from the container and an irradiation source arranged for irradiating the inner volume of the container. Generally preferred, the containers are sealed. Preferably, the irradiation source, e.g. a laser generator, is arranged with its beam path at an angle of 0° in the case of absorbance detector or in an angle equal to or below 180°, e.g. between 160° and 10° to the light path directed to the detector, e.g. in the case of a fluorescence or scatter light detector.

Alternatively, the device comprises at least two shear force generators, and irradiation source and an optical detector, both directed at a container provided for receiving the mixture of seed and native conformation prion protein. Preferably, the irradiation source, e.g. a laser generator, is arranged with its beam path at an angle of 0° or at an angle of 180° or below 180°, e.g. between 160° and 10° to the light path directed to the optical detector.

Generally, the optical detector can be a fluorescence detector or a scatter light detector or an absorbance detector.

Preferably, the optical detector is coupled to a computer having access to a databank that contains data on pre-determined amounts which are specific for a single shear-force intensity, preferably for at least two different shear-force intensities and specific for a seed from a specific source are contained. These data are provided in a databank on a data carrier, especially in a computer-based databank, and the comparison is carried out by a computer. Preferably, the databank contains the medical diagnosis for a specific neurodegenerative disease and/or a subtype thereof in association with the pre-determined data on amounts of aggregated conformation prion protein, each amount generated at one of at least two different shear-force intensities for each native conformation prion protein added and the diagnosis associated with the sample, and preferably additionally the specific source or sample to which the diagnosis pertains. As for some neurodegenerative diseases, the rate of amplification of aggregated conformation prion protein and/or the amount of aggregated conformation prion protein can differ in dependence on the point in time of the sample being taken during the disease progression, it is preferred that the databank contains information on the age of disease onset, sex of the mammal, duration of the disease, progression and/or severity of the disease, preferably at least data on the disease, subtype of the disease and severity of the disease. This embodiment can be used for generating a prediction or prognosis of the disease progression rate, based on the combination of seed-typing and seed-quantification in combination with other patient data. Accordingly, this information is set up in the databank in an arrangement according to this information.

The invention also relates to the databank, preferably computer-based, containing the medical diagnosis for a specific neurodegenerative disease and/or a subtype thereof in association with the pre-determined data on amounts of aggregated conformation prion protein, data on each amount generated at one of at least two different shear-force intensities for each native conformation prion protein added to the sample and the diagnosis associated with the sample, and preferably additionally data on the specific source or on the sample to which the diagnosis pertains, e.g. kind of sample material, storage conditions, solutions contacting the sample. As for some neurodegenerative diseases, the rate of amplification of aggregated conformation prion protein and/or the amount of aggregated conformation prion protein can differ in dependence on the point in time of the sample being taken during the disease progression, it is preferred that the databank contains information on the age of disease onset, sex of the mammal, duration of the disease, progression and/or severity of the disease, preferably at least data on the disease, subtype of the disease and severity of the disease. Further preferred, the databank contains data on the type of shear-force generator, on the temperature during application of shear-force, on the detector used for detecting the amount of aggregated prion protein. The databank, also described herein as a Reference Information Database, due to containing data on the amounts of aggregated prion protein generated for reference samples, for a sample allows the identification of a diagnosis by matching the amounts of aggregated conformation prion protein generated at at least one specific shear-force intensity to the data of the databank. As the presence of a specific control or standard substance during generation of data on the amounts of aggregated prion protein from a sample or reference sample is optional but not necessary, the databank has the advantage that the data contained therein preferably are absolute data, i.e. the data are independent from a specific control or standard substance. Accordingly, the process of the invention, especially when using the databank, also generates absolute results.

Preferably, the databank comprises data obtained by secondary analysis of aggregated conformation prion protein obtained by the application of one shear-force intensity by at least one of the following: size separation, e.g. chromatographically or electrophoretically, optionally with antibody detection, e.g. in a Western blot, structure sensitive spectroscopy, e.g. by infrared spectroscopy (IR), preferably Fourrier-transformed IR (FT-IR), NMR, especially $^{13}$C-NMR, and/or fluorescence spectroscopy, preferably after addition of a fluorescence dye being specific for aggregated conformation prion protein. Optionally, prior to the secondary analysis, the aggregated state prion protein obtained by the process can be contacted with proteinase. In this embodiment, the databank has the advantage of containing structure-related information on the aggregated state prion protein generated.

In a preferred embodiment, the databank comprises or is present in combination with the reference samples and/or aggregated conformation prion protein generated from the reference sample, preferably generated at one shear-force intensity, optionally at least two aggregated conformation prion proteins, each generated at one shear-force intensity. Preferably, the aggregated conformation prion protein was generated from the reference sample in at least two separate admixtures, each containing a different native conformation prion protein, e.g. one of Aβ, Tau and α-Synuclein. In this embodiment, the databank is suitable for a process for analysing or screening at least one compound for its effect on the generation of aggregated conformation prion protein from an admixture containing the compound, at least one native conformation prion protein and the reference sample or aggregated conformation prion protein generated at one shear-force intensity, acting as a seed.

The analytical process comprises the step of comparing the content of aggregated conformation prion protein generated by the different shear-forces to predetermined data on the content of aggregated conformation prion protein produced by subjecting the native conformation prion protein in a mixture with a seed to the same shear-forces. Therein, the predetermined data are contained in the databank described. The process for analysis for the presence of disease-related aggregated conformation prion protein in a biopsied mammalian sample, which preferably is a process for a differential in vitro analysis for identification and/or classification of a prion-related disease, comprises the steps of a) adding to the sample at least one native conformation prion protein, b) subjecting the mixture comprising the sample and the at least one native conformation prion protein obtained in step a) to at least one shear-force intensity that is controlled to have a uniform intensity having an intensity range of maximally 20% of one shear-force value for a pre-determined number of cycles of a pre-determined time of shear-force acting and a pre-determined resting phase, and c) following step b) determining the content of aggregated conformation prion protein for each of the shear-force intensities, comprising the step of d) comparing the content of aggregated conformation prion protein determined in step c) to pre-determined data on the content of aggregated conformation prion protein, which content was determined for native conformation prion protein in admixture with a reference sample subjected to the same shear-force intensity as in step b), wherein these data are provided in a databank which in association with these data contains the neurodegenerative disease diagnosis for the patient from which the reference sample originates. Therein, step d) of comparing the content of aggregated conformation prion protein determined for the biopsied mammalian sample in admixture with at least one native conformation prion protein to the data on the content of aggregated conformation prion protein pre-determined for a reference sample in admixture with at least one native conformation prion protein, each at the same controlled shear-force value, allows to assign the diagnosis associated with the pre-determined data to the biopsied mammalian sample.

Optionally, both for the sample and for the pre-determined data, the content of aggregated conformation prion protein generated by the application of one shear-force intensity can be determined as the rate of formation of aggregated conformation prion protein. This rate of generating aggregated conformation prion protein by the application of one shear-force intensity can e.g. be determined by measuring aggregated conformation prion protein following the resting phase of each cycle and/or by continuously measuring aggregated conformation prion protein during application of the shear-force. Accordingly, the detector is preferably coupled to a computer which is set up for determination of the rate of generation of aggregated conformation prion protein from measurement signals. Also in this embodiment the databank preferably is set up for storing pre-determined data on the rate of amplification of the aggregated conformation prion protein in dependence on the shear-force intensity applied and for storing in relation thereto data on the diagnosis given for the patient from whom the sample originates that is used for the pre-determination.

The rate of formation of aggregated conformation prion protein, the original content of aggregated conformation prion protein in the sample and/or a rate of dissociation of the aggregated conformation prion protein can be determined, especially separately for each shear-force intensity.

The formation of one aggregated conformation prion protein at one specific shear-force intensity is determined by the initial concentration of aggregated conformation prion protein ($p_{t=0}$), the kinetic rate of native conformation prion protein incorporation into the aggregated conformation prion protein ($k_+$) at one specific shear-force, the kinetic rate of native prion protein dissociation ($k_d$) from the aggregated conformation prion protein, and by the initial concentration of native conformation prion protein present in the admixture ($m_{t=0}$). The total amount of the detection signal determined for the content of aggregated stated prion protein (F), e.g. total fluorescence, is determined by the specific detection signal of the aggregated conformation prion protein ($f_s$). The parameter $p_{t=0}$ is determined by the original amount of one aggregated conformation prion protein present in a mammalian sample and by the mixing ratio of the patient sample with the solution of native conformation prion protein. The parameters $k_+$, $k_d$ and $f_s$ are chemical properties of the aggregated conformation prion protein. The parameter $m_{t=0}$ is pre-determined by the specific assays conditions.

The change of one aggregated conformation prion protein content (dp) over time (dt) at one specific shear-force intensity and at one specific time-point is determined by these parameters and by the present concentration of aggregated conformation prion protein (p) and the present concentration of native conformation prion protein (m). This is summarized by equation 1 (Eq. 1):

$$dp/dt = k_+ \cdot p \cdot m - k_d \cdot p \qquad \text{Eq. 1}$$

For example, the change of Thioflavin T Fluorescence ($dF_{sim}$) over time (dt) at one specific shear-force intensity and at one specific time-point is determined by the above mentioned parameters and by the present concentration of aggregated conformation prion protein (p) and the present concentration of native conformation prion protein (m). This is summarized by equations 2 and 3 (Eq. 2, Eq. 3):

$$dF_R/dt = f_s \cdot (dp/dt) \qquad \text{Eq. 2}$$

$$dF_R/dt = f_s \cdot (k_+ \cdot p \cdot m - k_d \cdot p) \qquad \text{Eq. 3}$$

Parameters $p_{t=0}$, $k_+$, $k_d$ and $f_s$ are independent variables which are used to approximate the observed signal for the content of aggregated conformation prion protein, e.g. the amount of fluorescence, between the time of the start of the reaction and the time of maximal fluorescence ($F_{obs}(t)$) by a non-linear regression analysis (R) using numerical or explicit solutions of Eq. 3. The nonlinear regression analysis minimizes the deviation of the approximated fluorescence ($F_R(t)$) from the observed fluorescence ($F_{obs}(t)$). The results of the regression analysis are approximated values for the parameters $p_{t=0}$, $k_+$, $k_d$ and $f_s$, wherein $k_+$ is specific for one shear-force intensity. Preferably, the values obtained for $p_{t=0}$, $k_+$, $k_d$ and $f_s$ can be associated to specific disease conditions in the databank, and they can e.g. be used to discriminate healthy from diseased people. Preferably, the values $p_{t=0}$, $k_+$, $k_d$ and $f_s$ which are determined from the observed time-resolved signal for the content of aggregated conformation prion protein at at least one shear-force intensity are part of the determined content of aggregated conformation prion protein for each of the shear-force intensities for the mixture of the sample and the at least one native conformation prion protein and for the pre-determined data of the mixture of the reference sample and the at least one native conformation prion protein. Accordingly, in the process the content of aggregated conformation prion protein is preferably determined in a time-dependent manner during subjecting the mixture to one shear-force intensity, e.g. it is determined as the time-resolved content, and that the rate of formation of aggregated conformation prion protein is determined by non-linear regression analysis from an approximation on the determined time-resolved content of aggregated conformation prion protein for each of the shear-force intensities.

Exemplary prion proteins are the proteins which in their aggregated state conformation cause or are present in the following diseases, with preferred amino acid sequences of the prion protein indicated: Scrapie in sheep (cellular prion protein PrP$^c$, major prion protein, accessible at http://www.uniprot.org/uniprot/P23907), bovine spongiform encephalitis in cattle (cellular prion protein PrP$^c$, major prion protein, accessible at http://www.uniprot.org/uniprot/P10279), chronic wasting disease in deer and elk (cellular prion protein PrP$^c$, major prion proteins, accessible at black deer: http://www.uniprot.org/uniprot/P47852, red deer: http://www.uniprot.org/uniprot/P67987, alpine musk deer: http://www.uniprot.org/uniprot/Q68G95), and Creutzfeld-Jacob disease, Gerstmann-Sträussler-Scheinker syndrome (cellular prion protein PrP$^c$, including mutant proteins thereof), fatal familial insomnia in humans (prion protein), wherein prion disease in humans, including Creutzfeld Jacob disease, Gerstmann-Sträussler-Scheinker (GSD) Syndrome, fatal familial insomnia (FFI) (major prion protein, accessible at http://www.uniprot.org/uniprot/P04156), GSD and FFI are exclusively associated with familial variants, CJD can be associated with familial variants, Alzheimer disease (amyloid beta, Aβ, especially Aβ of 40 (Aβ40) or 42 (Aβ42) amino acids, including mutant proteins thereof), especially Alzheimer disease or cerebral amyloid angiopathy in humans (beta amyloid (Aβ) A4 protein, accessible at http://www.uniprot.org/uniprot/P05067, especially the partial sequences beta-amyloid protein 42, and beta-amyloid protein 40, and also familial variants of the A4 protein), Alzheimer disease (tau and/or α-synuclein of human, mouse or rat, e.g. human alpha-synuclein accessible at http://www.uniprot.org/uniprot/P37840, mouse alpha-synuclein accessible at http://www.uniprot.org/uniprot/O55042 rat alpha-synuclein accessible at http://www.uniprot.org/uniprot/P37377, human tau, accessible at http://www.uniprot.org/uniprot/P10636 and corresponding tau sequences of mice and rats, accessible at http://www.uniprot.org/uniprot/P35637), Alzheimer in mouse or rat (mouse Aβ accessible at http://www.uniprot.org/uniprot/P12023; rat Aβ accessible at http://www.uniprot.org/uniprot/P08592, and tau accessible at http://www.uniprot.org/uniprot/P35637 and mouse α-synuclein, accessible at http://www.uniprot.org/uniprot/O55042, rat alpha-synuclein accessible at http://www.uniprot.org/uniprot/P37377), Parkinson (alpha-synuclein) and α-synucleopathies in humans (human alpha-synuclein accessible at http://www.uniprot.org/uniprot/P37840), Parkinson disease and α-synucleopathies in murine disease models (alpha-synuclein accessible at http://www.uniprot.org/uniprot/O55042) and Parkinson disease and synucleopathies in rat disease models (alpha-synuclein accessible at http://www.uniprot.org/uniprot/P37377), frontotemporal lobar dementia (TDP-43, accessible at http://www.uniprot.org/uniprot/Q13148), frontotemporal lobar dementia (tau, accessible at http://www.uniprot.org/uniprot/P10636), and corresponding tau sequences of mice and rats, frontotemporal lobar dementia (FUS, accessible at http://www.uniprot.org/uniprot/P35637), and corresponding FUS sequences of mice and rats, Amyotrophic Lateral Sclerosis (SOD1, accessible at http://www.uniprot.org/uniprot/P00441), Amyotrophic Lateral Sclerosis (TDP-43, accessible at http://www.uniprot.org/uniprot/Q13148), diabetes mellitus type 2 (amylin, accessible at http://www.uniprot.org/uniprot/P10997),), chorea Huntington (human huntingtin accessible at http://www.uniprot.org/uniprot/P42858, especially containing poly-Q expansions between amino acid sequence position 18 and 38), medullary carcinoma of the thyroid (calcitonin, accessible at http://www.uniprot.org/uniprot/P01258), cardiac arrhythmias, isolated atrial amyloidosis (atrial natriuretic factor, accessible at http://www.uniprot.org/uniprot/P01160), atherosclerosis (apolipoprotein A, accessible at http://www.uniprot.org/uniprot/P02647), rheumatoid arthritis (serum amyloid A, accessible at http://www.uniprot.org/uniprot/P0DJI8), aortic medial amyloid (medin, accessible at http://www.uniprot.org/uniprot/Q08431), prolactinomas (prolactin), familial amyloid polyneuropathy (transthyretin, accessible at http://www.uniprot.org/uniprot/P02766), hereditary non-neuropathic systemic amyloidosis (lysozyme, accessible at http://www.uniprot.org/uniprot/P61626), dialysis related amyloidosis (beta-2-microglobulin, accessible at http://www.uniprot.org/uniprot/P61769), Finnish amyloidosis (gelsolin, accessible at http://www.uniprot.org/uniprot/P06396), lattice corneal dystrophy (keratoepithelin, accessible at http://www.uniprot.org/uniprot/Q15582), cerebral amyloid angiopathy (beta-amyloid), also of the Icelandic type (cystatin, accessible at http://www.uniprot.org/uniprot/P01034), systemic AL amyloidosis (immunoglobulin light chain AL), sporadic inclusion body myositis (S-IBM), tauopathies involving the agglomeration of tau protein (human tau-protein accessible at http://www.uniprot.org/uniprot/P10636), Tauopathies involving the agglomeration of tau protein in murine disease models (mouse tau-protein accessible at http://www.uniprot.org/uniprot/P10637), Tauopathies involving the agglomeration of tau protein in rat disease models (rat tau-protein accessible at http://www.uniprot.org/uniprot/P19332)). Herein, tau protein includes isoforms, especially isoforms as described by Barghorn et al. (loc. cit.), human tau23 of 352 amino acids, lacking N-terminal inserts I1 and I2 between E45 and A103 and lacking R2 between V275 and V306, human tau37 of 381 amino acids, lacking N-terminal insert I2 between D74 and A103 and lacking R2 between V275 and V306, human tau39 of 410 amino acids, lacking R2 between V275 and V306, human tau24 of 383 amino acids, lacking N-terminal inserts I1 and I2 between E45 and A103, human tau34 of 412 amino acids, lacking N-terminal insert I2 between D74 and A103, human tau K19 of 98 amino acids containing amino acids Q244 to E372 but lacking R2 between V275 and V306, human tau K18 containing amino acids Q244 to E372, each in comparison to human tau40 of 441 amino acids (human tau isoform F accessible at http://www.uniprot.org/uniprot/P10636#P10636-8).

The amino acid sequences are accessible in protein databanks, e.g. in Uniprot. The amino acid sequence of the prion protein used in the process of the invention can optionally have an added synthetic or natural amino acid section, e.g. a detectable tag.

A preferred device for use in the process comprises at least one, preferably at least two separate shear-force generators, each controlled to apply one shear-force intensity to the admixture of sample and native conformation prion protein.

As the databank contains the amounts of aggregated conformation prion protein produced from reference samples for at least two specific shear-force intensities in association with at least the disease, the process can optionally be carried out without a positive control containing a known type and/or a known amount of aggregated conformation prion protein, and/or without a negative control containing no seed, i.e. native conformation prion protein only.

The invention is now described in greater detail by way of examples with reference to the figures that show in FIGS. 1 to 6 fluorescence measurements specific for the amplification of the aggregated conformation of prion protein at different shear-force intensities for samples of known diagnosis, FIGS. 7-10 fluorescence measurements specific for the amplification of the aggregated conformation of prion protein at different shear-force intensities for samples from post mortem brain samples, FIG. 11 a schematic overview of an embodiment of the process, FIG. 12 a schematic overview of an embodiment of the process, FIG. 13 a schematic cross-section of a preferred device for use in the process, FIG. 14 an exploded schematic view of the device of FIG. 13, FIG. 15 a schematic view of a device, FIG. 16 a schematic view of an embodiment of the device, FIG. 17 a schematic cross-section along line A1 of FIG. 16, and FIG. 18 a schematic cross-section along line A2 of FIG. 17.

Example: Amplification of Aggregated State Conformation at Different Shear-Force Intensities As samples, a 1:50 volume portion of brain homogenate was used and mixed with 2 mg/ml alpha-synuclein as the native conformation prion protein. The brain homogenate was prepared by homogenization in cold phosphate-buffered saline (PBS) containing 0.5% Triton X-100 and 1× complete EDTA-free protease inhibitor cocktail (Roche, Cat. No. 11873580001) using 20 strokes with a dounce homogenizer on ice. Brain samples were post-mortem from one healthy control (NEG.) and four different synucleopathy disease patients: Idiopathic Parkinson's Disease (IPD), Parkinson's Disease with Dementia (PDD), Dementia with Lewy-Bodies (DLB), Muliple System Atrophy (MSA). The suspension was clarified by centrifugation at 2000×g for 45 s, and the supernatant was used.

As another sample, 360 μl human cerebrospinal fluid (CSF), stored at −80° C. were mixed with 40 μl cold 10×PBS containing 0.5% Triton X-100 and 1× complete EDTA-free protease inhibitor cocktail and clarified by centrifugation at 2000×g for 45 s, giving the supernatant as human cerebrospinal fluid extract (CSFE). In this example the CSF sample was post-mortem from the same patient of Parkinson's disease with dementia (PDD) that was used above.

The native conformation prion protein was recombinantly expressed human alpha-synuclein of approx. 5.0 mg/ml water, stored at −80° C. and thawed at 37° C. at very mild agitation. The protein concentration was adjusted to 2.22 mg/ml using sterile-filtered water and 13.5 ml thereof were mixed with 1.5 ml of 10× concentrated PBS to yield 2.0 mg/ml human alpha-synuclein in PBS.

On ice, 15 ml of 2.0 mg/ml human alpha-synuclein in PBS were combined with 300 μl brain homogenate supernatant, or alternatively with 300 μl CSFE. Of this mixture, twelve identical aliquots of 1.2 ml each were filled into 1.5 ml sealed polypropylene test tubes (SureLock, Eppendorf). Into each test tube, one rotary shearing device having a rotor of 2.00 mm within a tube at a gap width of 0.30 mm was inserted. These assemblies were incubated at 37° C. for 15 min. Shear-force was applied by rotating the rotors with control of the rotating rate to at maximum 1% from the rate set for 5 s with a subsequent resting phase of 295 s for a total of 22 h. The rotating rates used are indicated in FIGS. 1 to 9. Generally, the device corresponded to WO 2012/110570.

Samples of 20 μl were taken from each reaction mixture at time 0 h, 3 h, 6 h, 9 h, 12 h, and at 22 h under shear-force. The amplification of aggregated state conformation was determined by fluorescence spectroscopy of 15 μl of the sample taken after mixing with 135 μl Thioflavin T stock solution (30 μM Thioflavin T in PBS buffer solution) with excitation at 450 nm (bandwidth 10 nm) and detection at 482 nm (bandwidth 20 nm).

The brain samples originated from patients diagnosed with the following Parkinson syndromes: Idiopathic Parkinson Disease (IPD), ICD-10: G20
- Dementia in Parkinson's disease (PDD), ICD-10: G20, F02.3
- Multisystem Atrophy (MSA), ICD-10: G90.3:
- Dementia with Lewybodies (DLB), ICD-10: G31.8, F02.3
- Healthy Control (NEG.), and the CSF sample originated from a patient diagnosed with
- Dementia in Parkinson's disease (PDD), ICD-10: G20, F02.3

For diagnosis, the ICD-10 codes (available at www.ICD-code.de, at http://apps.who.int/classifications/icd10/browse/2010/en#, at http://www.who.int/classifications/icd/en/, and at http://www.who.int/classifications/icd/en/GRNBOOK.pdf) were used.

In detail, F00 Dementia in Alzheimer's disease: Alzheimer disease (AD) is a primary degenerative cerebral disease of unknown etiology with characteristic neuropathological and neurochemical features. The disorder is usually insidious in onset and develops slowly but steadily over a period of several years. Associated with the deposition of seed of abeta protein, tau protein, and sometimes synuclein protein
- F00.0*, G30.0*: Dementia in Alzheimer's disease with early onset. Dementia in Alzheimer disease with onset before the age of 65, with a relatively rapid deteriorating course and with marked multiple disorders of the higher cortical functions. Includes: (i) Alzheimer disease, type 2; (ii) Presenile dementia, Alzheimer type; (iii) Primary degenerative dementia of the Alzheimer type, presenile onset.
- F00.1*, G30.1*: Dementia in Alzheimer's disease with late onset. Dementia in Alzheimer disease with onset after the age of 65, usually in the late 70s or thereafter, with a slow progression, and with memory impairment as the principal feature. Includes (i) Alzheimer disease, type 1; (ii) Primary degenerative dementia of the Alzheimer type, senile onset; (iii) Senile dementia, Alzheimer type.
- F00.2*, G30.8*: Dementia in Alzheimer's disease, atypical or mixed type. Atypical dementia, Alzheimer type
- F00.8, G30.9: Dementia in Alzheimer's disease, unspecified F02 Dementia in other diseases classified elsewhere. Cases of dementia due, or presumed to be due, to causes other than Alzheimer disease or cerebrovascular disease. Onset may be at any time in life.
- F02.0*, G31.0*: Dementia in Pick's disease (Frontotemporal lobular Dementia, FTD). A progressive dementia, commencing in middle age, characterized by early, slowly progressing changes of character and social deterioration, followed by impairment of intellect, memory, and language functions, with apathy, euphoria and, occasionally, extrapyramidal phenomena.
- F02.2*, G10*: Dementia in Huntington's disease (HD). A dementia occurring as part of a widespread degeneration of the brain. The disorder is transmitted by a single autosomal dominant gene. Symptoms typically emerge in the third and fourth decade. Progression is slow, leading to death usually within 10 to 15 years. Includes: Dementia in Huntington chorea
- F02.3*, G20*: Dementia in Parkinson's disease (PDD): dementia developing in the course of established Parkinson disease. No particular distinguishing clinical features have yet been demonstrated. Includes (i) Hemiparkinsonism, (ii) Paralysis agitans, (iii) Parkinsonism or Parkinson disease (NOS (not otherwise specified), idiopathic, primary)
- F02.3*, G31.82: Lewy body Dementia (DLB), Lewy Body Disease (LBD). A progressive degenerative dementia. Persons with LBD will show markedly fluctuating cognition. Persistent or recurring visual hallucinations with vivid and detailed pictures are often an early diagnostic symptom.

A81 Atypical virus infections of central nervous system. Prion diseases of the central nervous system.
- A81.0*, F02.1*. Dementia in Creutzfeldt-Jakob disease. A progressive dementia with extensive neurological signs, due to specific neuropathological changes that are presumed to be caused by a transmissible agent. Onset is usually in middle or later life, but may be at any adult age. The course is subacute, leading to death within one to two years.
- A81.8: Other atypical virus infections of central nervous system: Kuru
- A81.9: Atypical virus infection of central nervous system, unspecified: Prion disease of central nervous system.

Amyloidosis:
168.0* Cerebral amyloid angiopathy (E85.−+)
[Possibly to be extended]

Parkinson Syndromes:
G20: Idiopathic Parkinson Disease (IPD)
G20, F02.3: Dementia in Parkinson's disease (PDD)
G90.3: Multisystem Atrophy (MSA)
G31.8, F02.3: Dementia with Lewybodies (DLB)

Motor Neuron Disease:
G12.2: Motor neuron disease: includes (i) Familial motor neuron disease and (ii) Amyotrophic Lateral sclerosis (ALS).

FIGS. 1-6 show the fluorescence detected in 3 independent repetitions of the examples. In FIG. 1, the sample was BN449-PDD, in FIG. 2 BN379-IPD, in FIG. 3 BN175-MSA, in FIG. 4 BN526-DLB, in FIG. 5 BN449-PDD total CSF, and in FIG. 6 BN276 Healthy Control.

The results show that in the healthy control (NEG.), no aggregated conformation prion protein was generated. All the samples from the patients diagnosed with Parkinson syndromes resulted in the generation of amplification that was dependent on the shear-force intensity (rotation rate, application time, resting time and cycle number) and dependent on the origin of the sample. The process was highly reproducible in three independent experiments performed on the same brain tissues.

In FIGS. 1-10, the shear-force intensities are given as rpm of the rotary shear-force generator on the X-axis, the amounts of aggregated conformation prion protein detected are given on the Y-axis with the individual curves for given for the time points indicated on the right (h application of shear-force intensities).

Figure 5:
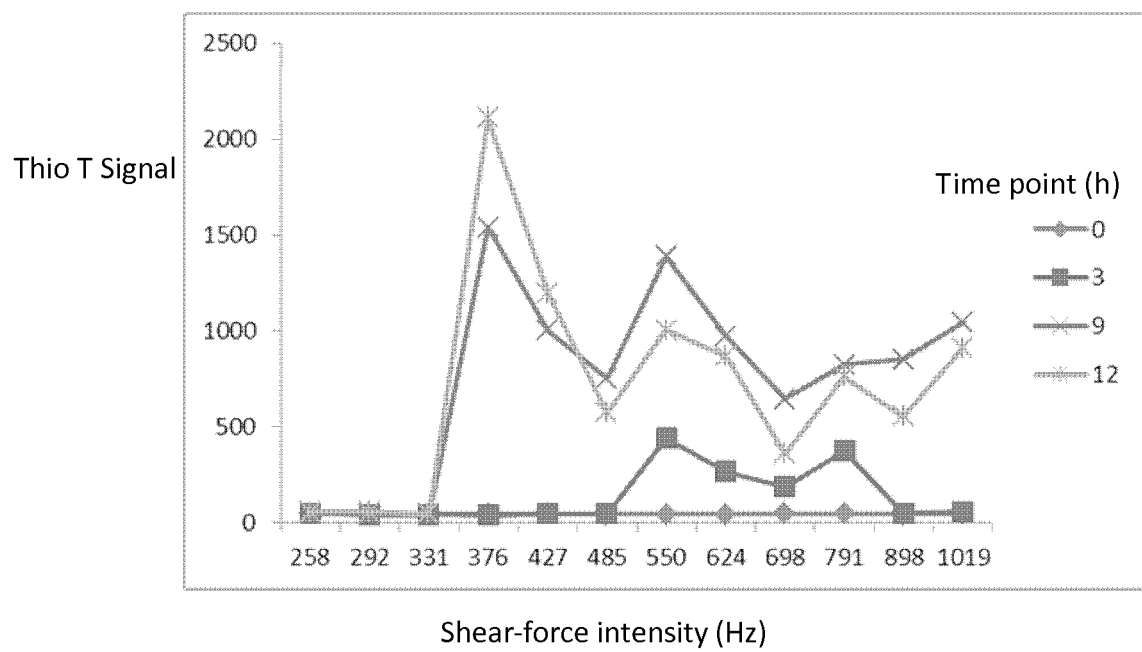
Figure 6:
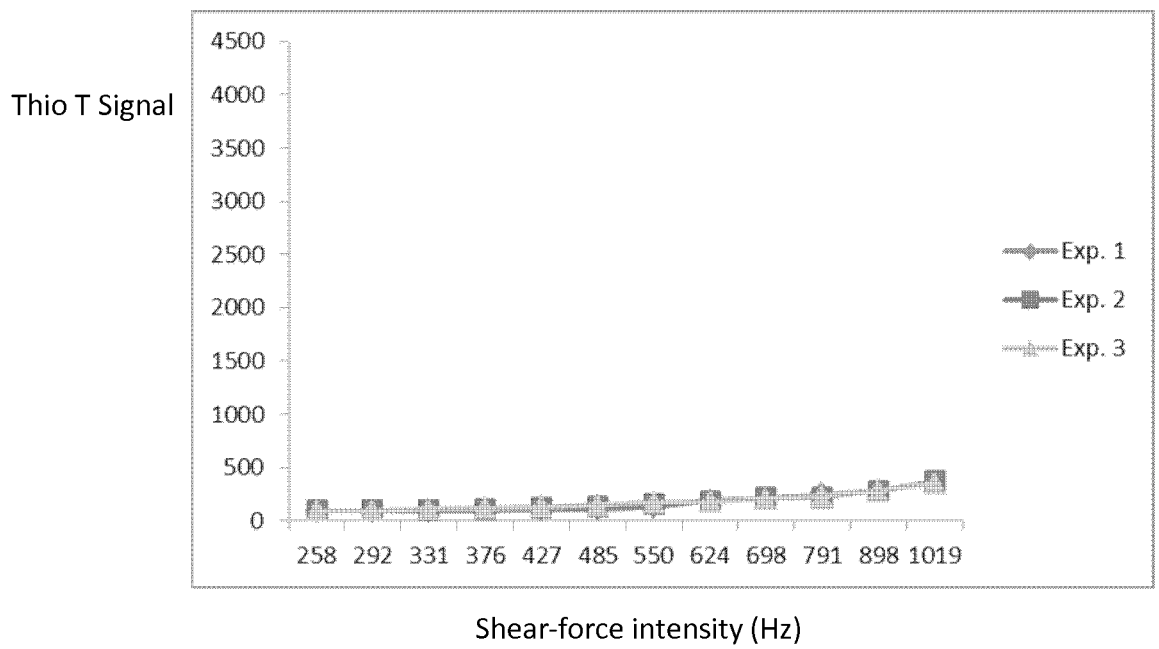

In FIGS. 1-4 and 6, the contents of aggregated conformation prion protein generated at a pre-determined application of one shear-force intensity each is depicted, showing a specific pattern of amplification for each sample for the shear-force intensities. In FIG. 5, the contents of aggregated conformation prion protein at 0 h, and generated at 3 h, 9 h and 12 h, respectively, are depicted, showing the different rates of amplification at different shear-force intensities. For the process of the invention it is therefore generally preferred that the shear-force intensity is pre-determined and the same for the sample and for pre-determined contents, e.g. the shear-force intensity can generally be pre-determined for shear-force applied, duration of shear-force application, duration of resting phase for each cycle, and repetition number of cycles.

The results show that the process of the invention differentiates between samples of different pathologies and between subtypes, e.g. specific disease presentation of individual patients.

Figure 7:
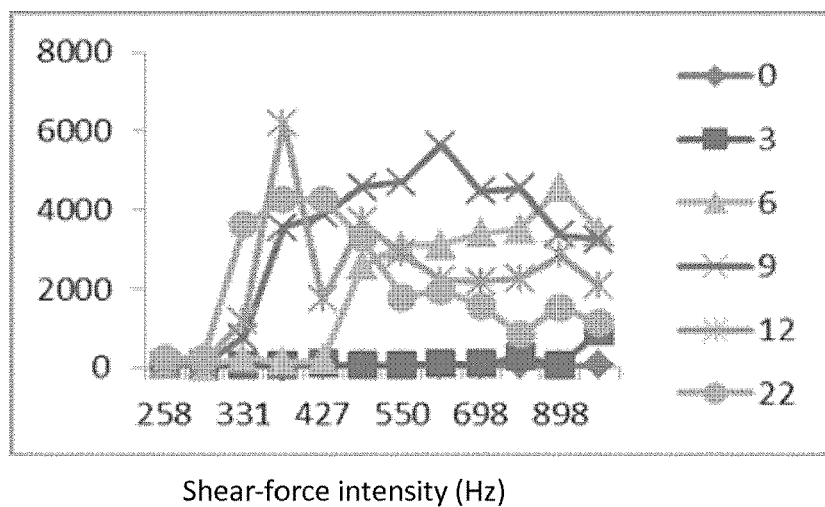
Figure 8:
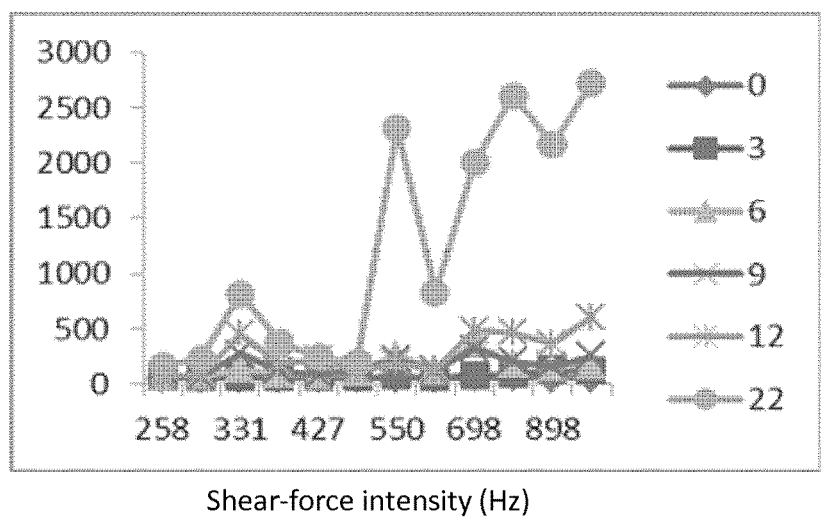
Figure 9:
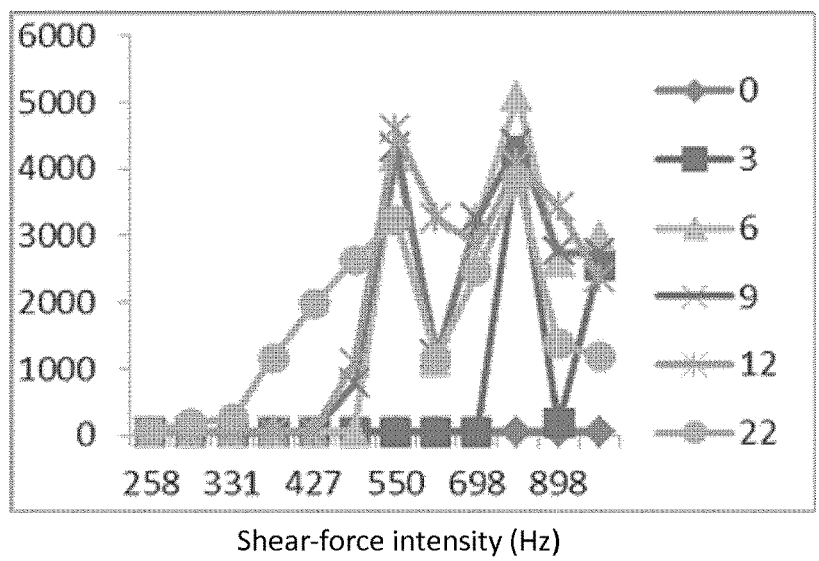

FIGS. 7-9 show results for the same process conditions for post mortem brain (BN) samples, wherein numbers designate individual samples. In contrast to the samples of FIGS. 1-6, the disease status of patients from whom the samples of FIGS. 7-9 originate is unknown to the persons involved in performing the analytical process. In these Figures, the content of aggregated prion protein generated at different time points is indicated.

The results depicted in FIGS. 7-9 show that the amplification greatly varies between samples and between points in time of shear-force application.

Figure 10:
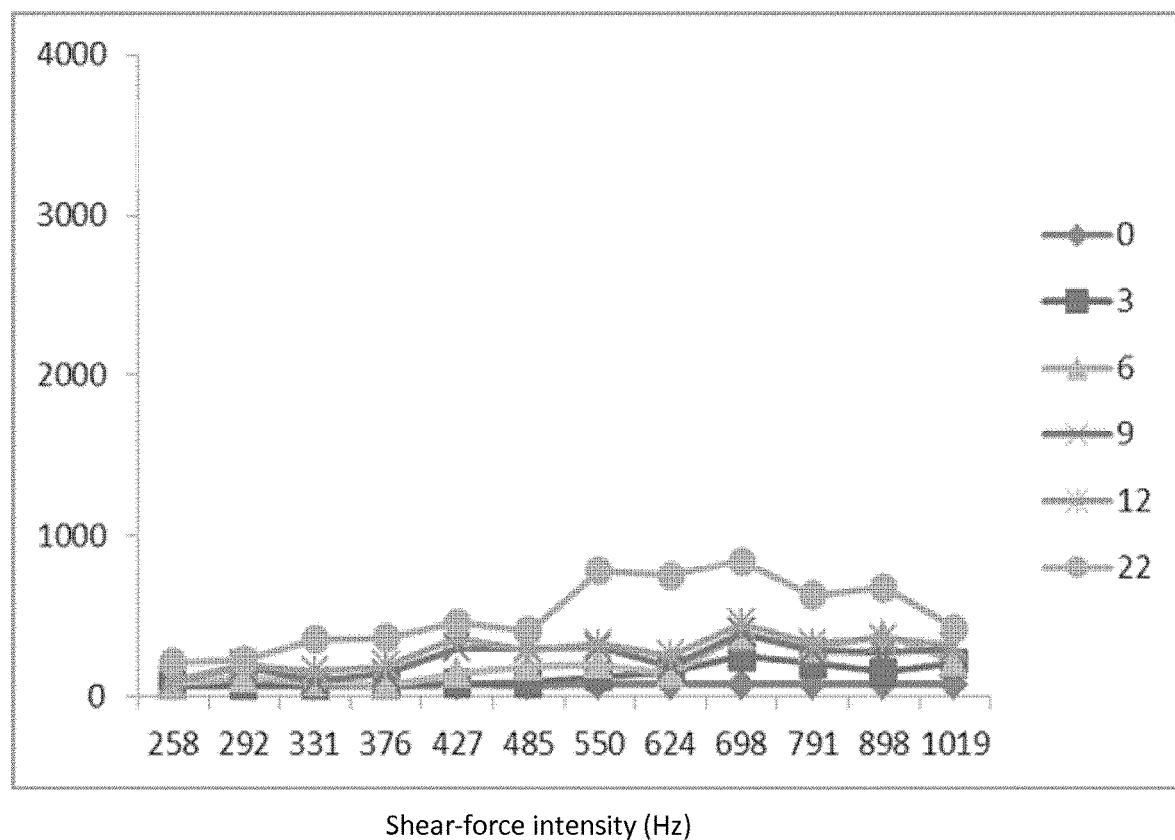
Figure 11:
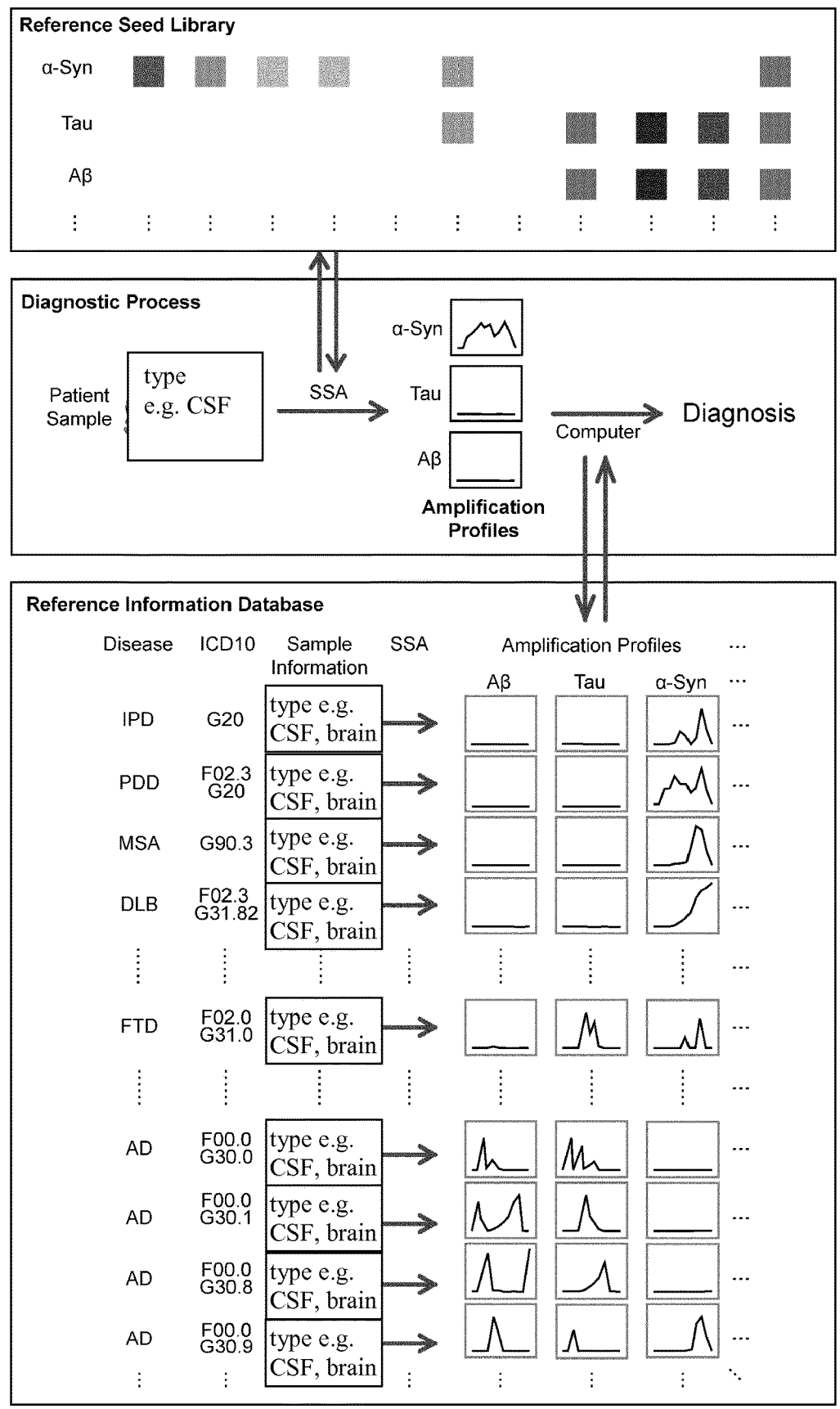
Figure 12:
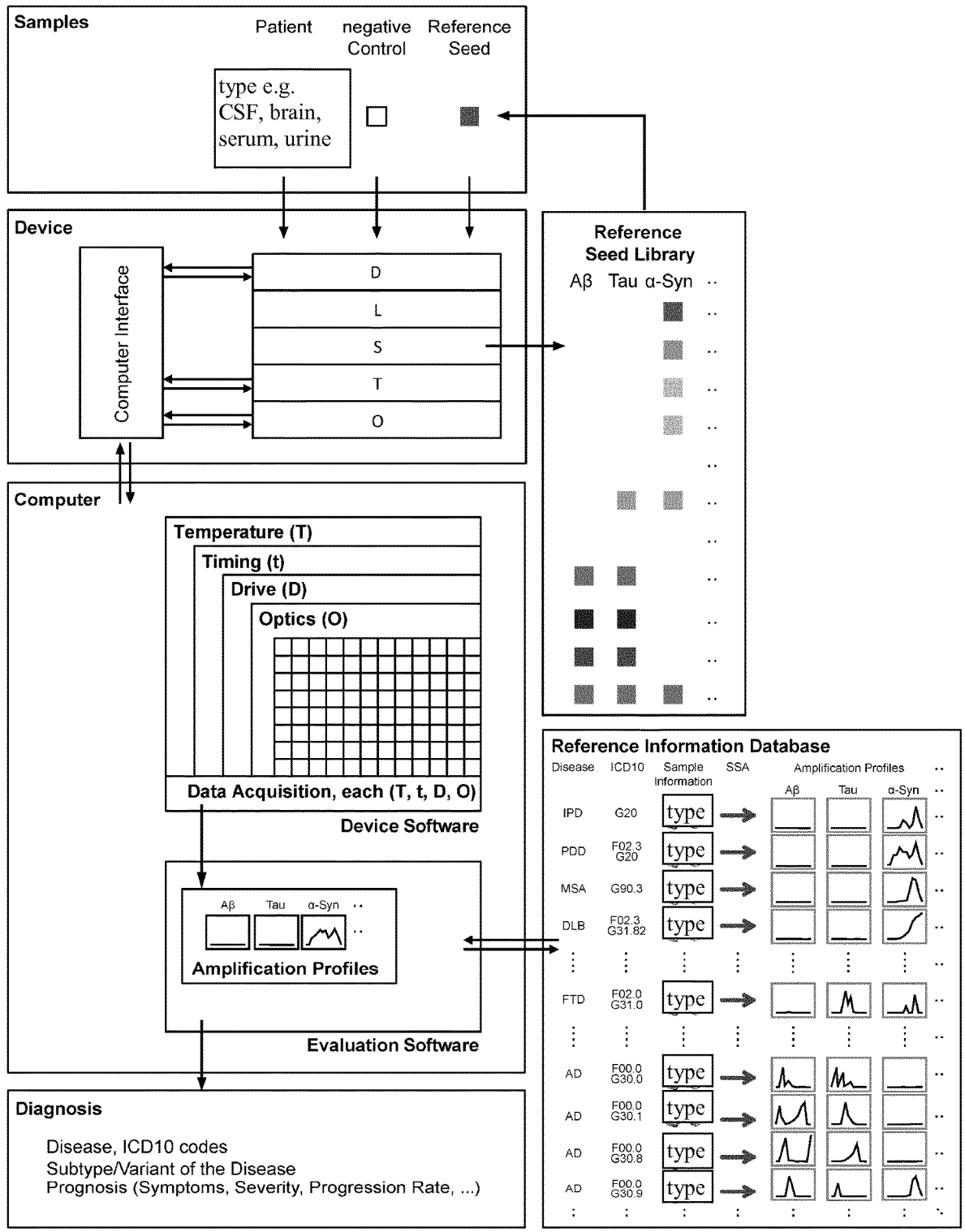
Figure 13:
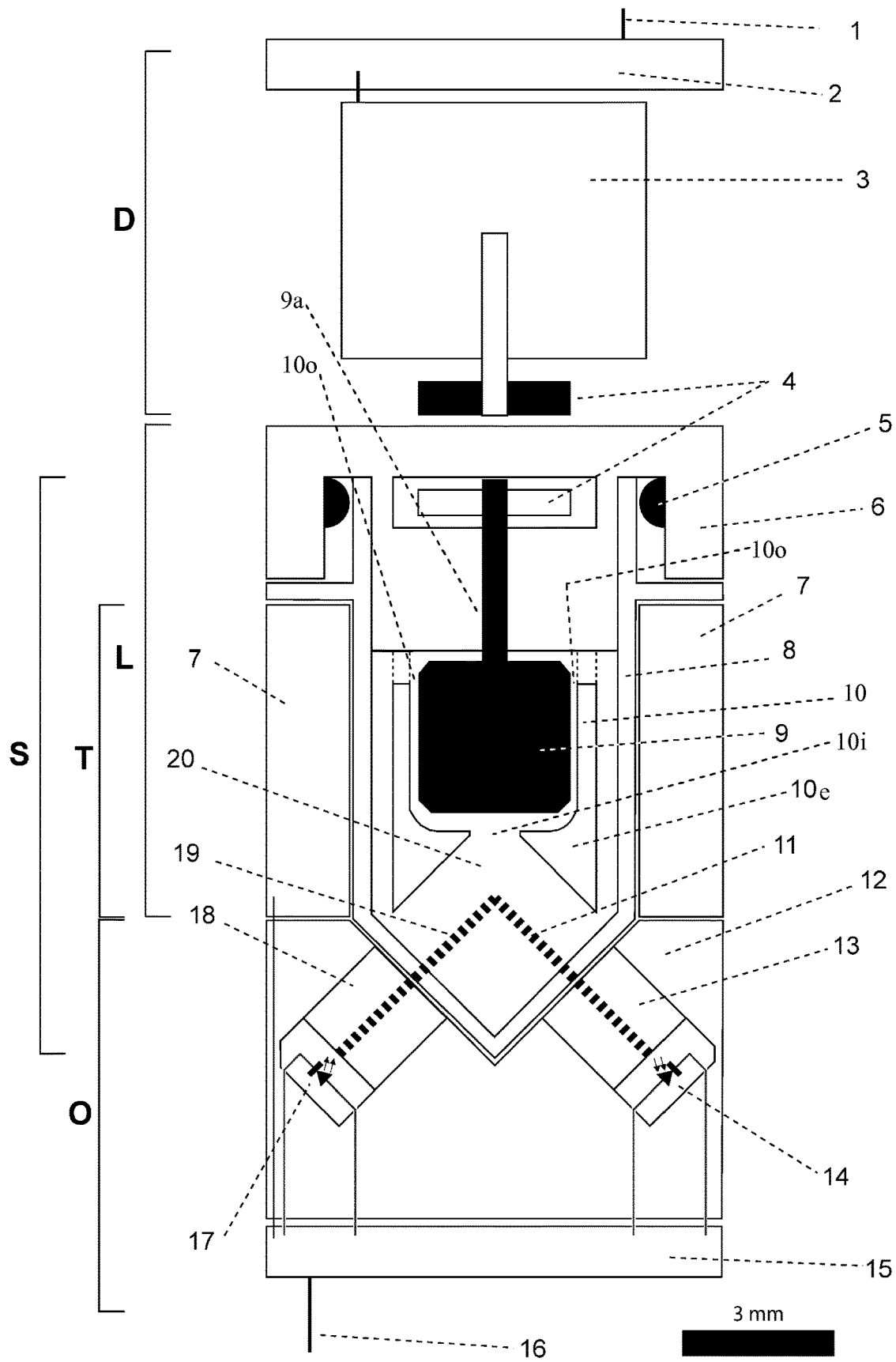
Figure 14:
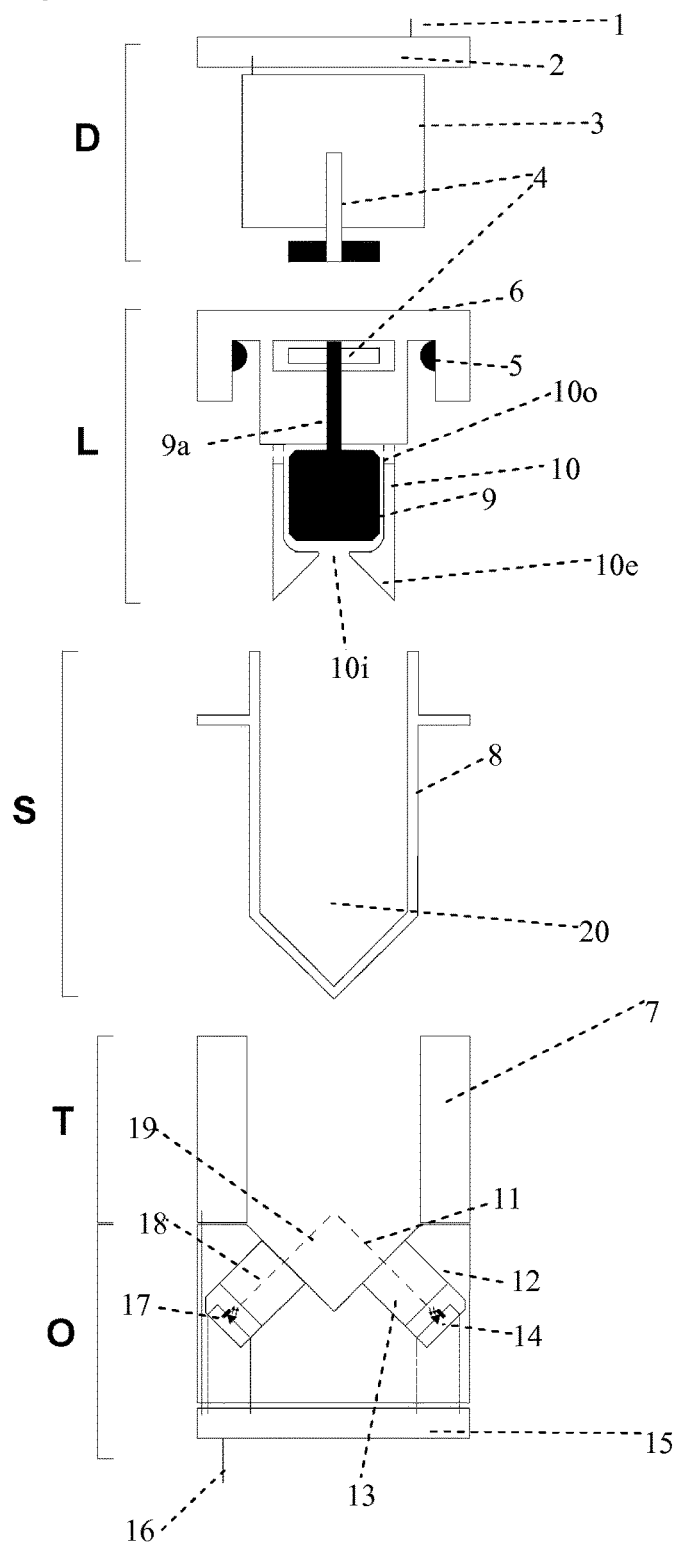
Figure 15:
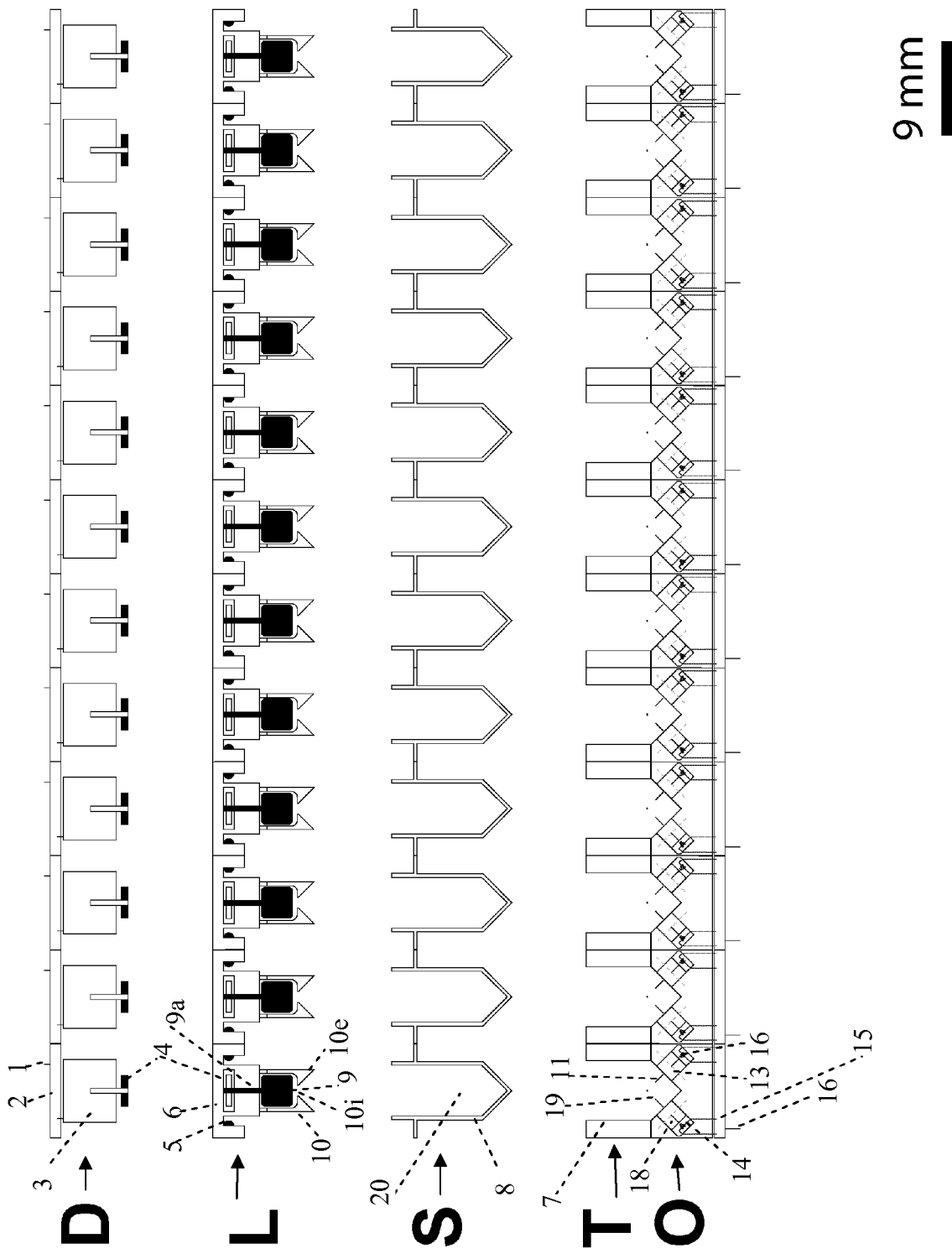
Figure 16:
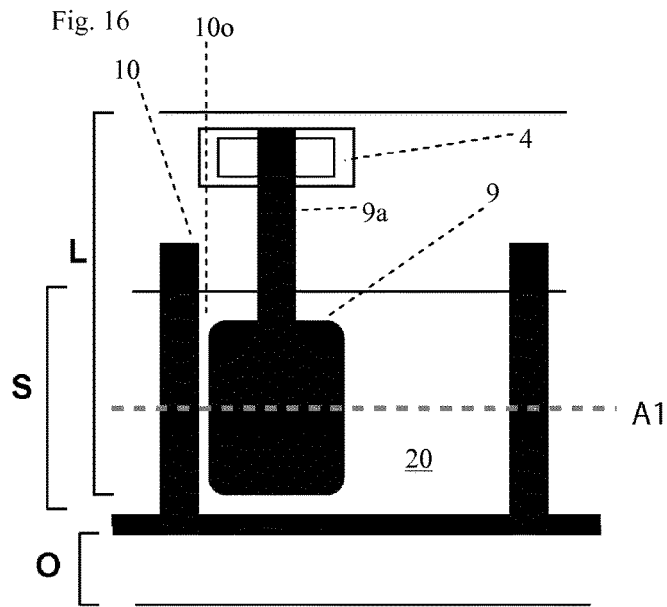
Figure 17:
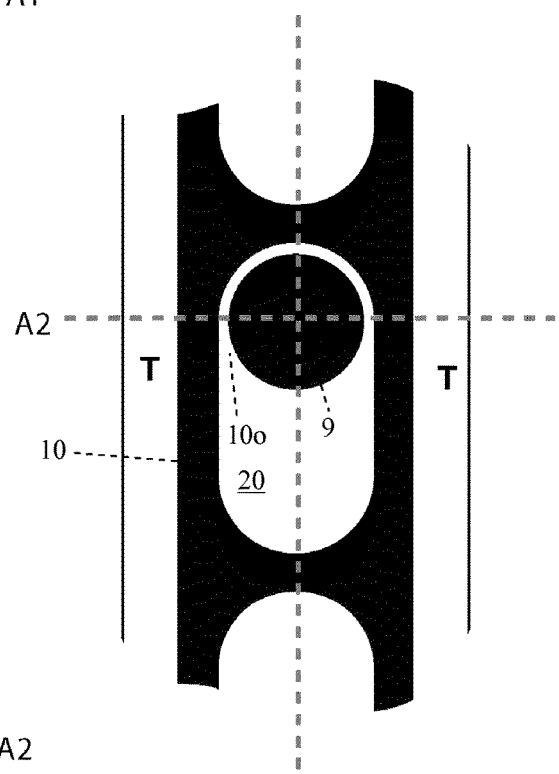
Figure 18:
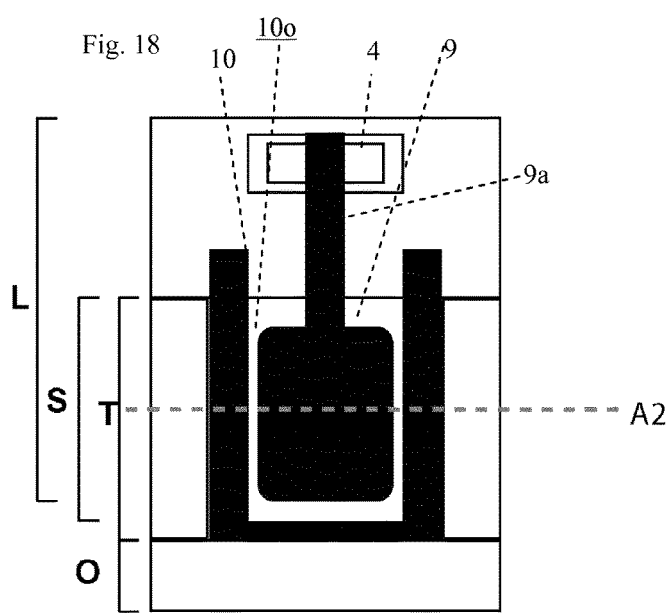

FIG. 10 shows the amount of aggregated conformation prion protein from an admixture of a post mortem sample of a brain histologically determined as Alzheimer and human α-synuclein as the native conformation prion protein. The result shows that the Alzheimer sample which was diagnosed to contain Aβ and tau protein aggregates when subjected to specific shear-force intensities did not significantly induce the generation of aggregated conformation prion protein from the native conformation α-synuclein. This results demonstrates that at least for this Alzheimer sample, generation of aggregated conformation prion protein from a native conformation prion protein is specific for the sample.

A comparison of the amplification of aggregated prion protein at single shear-force intensities, i.e. for different rotation rates at the same cycles for a total of 22 h allows to identify similar patterns of amplification, preferably an identification of the unknown sample according to similarities of the amplification pattern generated from a sample of known diagnosis. In this process, the sample of known diagnosis serves as a reference sample. In detail, the samples of FIGS. 8 and 9 show a similar amplification pattern at specific shear-force intensities (22 h) as the IPD sample of FIG. 2.

Therefore, it is assumed that the process can differentiate samples according to the progression of accumulation of aggregated prion protein during disease.

FIG. 11 schematically shows an overview of the process for analysis. Reference samples, e.g. post mortem brain tissue samples, serum, CSF or urine, each in association with the specific diagnosis for a neurodegenerative disease are provided as a library of reference seeds (Reference Seed Library). In the library, the reference samples can be assigned to the respective prion protein, represented by alpha-synuclein (α-Syn), tau (Tau) or amyloid beta (Aβ). For the reference samples, pre-determined data on the amounts of aggregated conformation prion protein is generated by application of specific shear-force intensities (SSA) from an admixture containing reference sample and native conformation prion protein. The measurement can be by optical determination of the amounts of aggregated conformation prion protein in Western blots or using an optical detector receiving irradiation from the admixture. As indicated by the double arrows between the Reference Seed Library and the databank Reference Information Database, the data on the detected amounts (Amplification Profiles) of aggregated conformation prion protein in respect of each shear-force intensity are stored in a computer and stored in a databank (Reference Seed Library) in association with the respective specific diagnosis (Disease, IPD, PDD, MSA, DLB, FTD, AD), preferably including at least one subtype (G20, F02.3, G90.3, G31.82, G31.0, F00.0, G30.0, G30.1, G30.8, G30.9) according to a classification (ICD10). The databank (Reference Information Database) therefore for each reference sample (Sample Information) in association with the specific disease, preferably its subtype, for the native conformation prion protein used (Aβ, Tau, α-Syn) contains the amounts of aggregated conformation prion protein for each shear-force intensity (Amplification Profiles).

As indicated by the double arrows between the Diagnostic Process and the Reference Seed Library, patient samples can be integrated into the reference samples (Reference Seed Library) once the diagnosis associated with the sample is known.

As generally preferred, the sample to be analysed (Patient Sample) in admixture with the same native conformation prion protein (separated admixtures for each of α-Syn, Tau and Aβ) as at least one reference sample of the Reference Seed Library is subjected to the same at least one shear-force intensity (SSA), and amounts of aggregated conformation prion protein are measured. Generally preferred, the sample to be analysed is of the same type as the reference sample, e.g. blood serum, lymph fluid, urine, CSF or a tissue sample.

The amount of aggregated conformation prion protein generated at specific shear-force intensities generated for a sample (Patient sample) is compared to the amount of aggregated conformation prion protein generated at the same shear-force intensities for the same native conformation prion protein (Aβ, Tau, α-Syn) each (Computer), allowing the identification (Diagnosis) of the diagnosis associated to the reference sample in the databank (Reference Information Database) by this comparison.

FIG. 12 in addition to FIG. 11 shows that preferably for each application of a shear-force intensity in addition to a sample to be analysed (Patient), native prion protein only, i.e. without a seed (negative Control) and a reference sample (Reference Seed) as a positive control can optionally be used in the process in parallel to the sample. The reference sample can e.g. be taken from the Reference Seed Library. Generally, the reference sample can be an aggregated conformation prion protein produced by application of one shear-force intensity to an admixture of one patient sample of known disease with native conformation prion protein, preferably followed by at least one further application of the same shear-force intensity to an admixture of an aliquot of the resultant product with the same native conformation prion protein.

Further, FIG. 12 shows that preferably for each application of a shear-force intensity to a sample or reference sample, at least one of the following data is stored: the specific shear-force generator or its drive D, preferably including the frequency generated by its drive D, the type of lid L, the type of sample compartment S, e.g. comprising the lid L, the thermostat T and the optical detector O, the current temperature and/or the specific temperature control element T and/or the type and/or specific optical detector O, including the optical measurement data are stored, e.g. using an interface (Computer Interface) coupled to each shear-force generator of the device and coupled to the computer (Computer) for transmitting the data. As further preferred, FIG. 12 shows that for measuring the amount of aggregated conformation prion protein, the computer is set up to store the temperature, time course (Timing, t), the shear-force generator (Drive, D), and the optical detector (Optics, O) for each application of a shear-force intensity, preferably including storing the time course of the detected amounts of aggregated conformation prion protein, e.g. in the form of amplification profiles for each native conformation prion protein in an admixture using e.g. a programme for storing these data (Device Software). Further, the device optionally comprises a a programme (Evaluation Software) for generating from these data which are measured and stored during the application of at least one shear-force intensity the amounts of aggregated conformation prion protein, each for the combination of specific native conformation prion protein of the admixture (Aβ, Tau, α-Syn), with the measured values for shear-force intensity, temperature, time-course of the application of shear-force intensity, specific shear-force generator and/or specific optics, e. g. detector. The evaluation software has access to the databank. The device contains or has access to the databank comprising pre-determined amounts of aggregated conformation prion protein generated at at least one shear-force intensity for reference samples (Reference Information Database), and the computer is set up to compare the amplification profiles generated for samples for each shear-force intensity (double arrows between Computer and Reference Information Database), allowing the association of a disease, preferably including its subtype, stored for a reference sample to the sample analysed. The computer is optionally set up to edit this diagnosis (Diagnosis).

FIGS. 13 and 14 show cross-sections of a preferred shear-force generator for use in the invention. By way of a connection 1, e.g. a data transfer line to a computer (not shown), a drive control unit 2 is controlled by the computer. The drive control unit 2 controls the drive motor 3 to a uniform rotation frequency. The drive control unit 2 and the drive motor 3 can also be termed drive D. The rotor 9 is arranged on an axle 9*a* that is connected to the drive motor 3 by a coupling 4, which preferably is a magnetic coupling. The rotor 9 is arranged within a container 8 and a stator 10 is arranged between the rotor 9 and the container 8. The stator 10 is arranged with a spacing to rotor 9, which preferably is a uniform spacing to the radial outer surface of rotor 9, e.g. forming a channel of ring-shaped cross-section, and stator 10 is arranged with a spacing to container 8. Preferably, stator 10 is mounted on the lid section L, also containing a bearing for axle 9*a*. Optionally, lid section L contains drive motor 3 and drive control unit 2. Stator 10 preferably has extensions 10*e* opposite the axle 9*a* carrying rotor 9, which extensions 10*e* form a funnel having an inlet 10*i* and reducing the free inner volume of container 8 in the region between the end of rotor 9 opposite the axle 9*a* and container 8. The inlet 10*i* of the stator 10 is preferably arranged coaxially to rotor 10 and forms the narrow exit of the funnel formed by extensions 10*e*, guiding liquid to the front surface section of rotor 9, allowing a pumping action by rotor 9 to move liquid into the spacing between the radial surface of rotor 9 and stator 10. Opposite the inlet 10*i*, the outlet opening 10*o* has at least the cross-section of the spacing between rotor 9 and stator 10.

The container 8 provided for receiving a sample 20 is arranged within a housing 7, which preferably at least sectionally is a thermostat T, preferably having form fit to the container 8. Preferably, the thermostat T for each container 8 has a temperature sensor and is independently computer-controlled. The open end of the container 8 is closed by a lid 6 and a seal 5. As shown, the section of housing 7 embracing the section of container 8 between extensions 10*e* of stator 10 and the bottom of the container 8 opposite its opening is provided with a light source 17 arranged to irradiate the inner volume of the container 8 and an optical detector 14 arranged to receive irradiation exiting the inner volume of the container 8, wherein preferably the beam path of the light source 17 crosses the beam path of the optical detector 14 in the area between the inlet 10*i* and the bottom of the container 8. The beam path 19 generated by the light source 17 can cross the exiting beam path 11 towards the optical detector 14 e.g. at an angle of 90°. Both the light source 17 and the optical detector 14 are coupled to a computer for control of the light source 17 and for receiving measurement signals from the detector 14. In the exiting beam path 11, a wavelength discriminator 13, e.g. an optical filter can be arranged. In the beam path 19 generated by the light source 17, a wavelength discriminator 18, e.g. an optical filter can be arranged. The housing 12 for the detector 14 and/or for the light source 17 has a dataline 16 for transmitting data on irradiation and measurement signals to a computer. Optionally, a control unit 15 for controlling the thermostat T and/or the light source 17 is arranged at the housing 12. Preferably, housing 12 containing the light source 17, optionally provided with a wavelength discriminator 18, and optical detector 14, optionally provided with a wavelength discriminator 13, form an integrated optical unit O. The optical unit O can be mounted releasably to thermostat T and to adjacent lid section L, wherein these elements form a recess for receiving a portion of container 8.

The scale indicated in FIGS. 13 and 14 is an exemplary scale, indicating that preferably each container 8 is provided with an individual controlled shear-force generator comprising a rotor 10 within a stator 9, a thermostat T, a light source 17 and a detector 14 and a controlled drive motor 3 within a scale of 7 to 12 mm, preferably 9 mm, for arrangement in a row or grid. FIG. 15 shows a generally preferred arrangement of at least two, e.g. of 8 or 12 containers that are connected to one another, each provided with a separate shear-force generator comprising a drive D and a lid section L, wherein drives D and lid sections L as well as thermostats T and optical units O, respectively are connected to one another in the same spacing for arrangement around spaced-apart coupled containers 8.

FIG. 16 shows another embodiment, wherein the shear-force generator is formed of a rotor 9 and stator 10 consisting of a wall section of the container 8. The wall section of the container 8 forming the stator 10 is e.g. arranged for a portion, e.g. at least 1° to 270°, e.g. for 30° to 180° about the circumference of the rotor 9 at a constant distance. As shown in FIG. 16, the rotor 9 is preferably arranged asymmetrically within container 8, leaving a free inner volume section for optical detection.

The container 8 can e.g. have a circular, oval or egg-shaped cross-section, and the rotor 9 can be arranged within a part of the cross-section having a smaller or larger diameter.

FIGS. 17 and 18 show that the container 8 preferably forms a stator 10 arranged at a constant distance from the rotor 9 for a portion about the circumference of the rotor 9, wherein this distance forms the smallest passage between rotor 9 and stator 10. Accordingly, the surface of rotor 9 preferably is parallel to the stator 10 for a portion of the circumference of the rotor 9.

REFERENCE NUMERALS

| | |
|---|---|
| 1 | connection |
| 2 | drive control unit |
| 3 | drive motor |
| 4 | coupling |
| 5 | seal |
| 6 | lid |
| 7 | housing |
| 8 | container |
| 9 | rotor |
| 9a | axle |
| 10 | stator |
| 10e | extensions |
| 10o | outlet opening |
| 10i | inlet |
| 11 | exiting light path |
| 12 | housing containing optical detector and light source |
| 13 | wavelength discriminator |
| 14 | optical detector |
| 15 | control unit |
| 16 | dataline |
| 17 | light source |
| 18 | wavelength discriminator |
| 19 | beam path from light source |
| 20 | sample |
| D | drive |
| L | lid section |
| T | thermostat |
| S | sample compartment |
| O | optical unit |

The invention claimed is:

1. A process for analysis for the presence of neurodegenerative prion-protein aggregation disease-related aggregated conformation prion protein in a biopsied mammalian sample, the disease being one of Idiopathic Parkinson's Disease (IPD), Parkinson's Disease with Dementia (PDD), Dementia with Lewy-Bodies (DLB) or Multiple System Atrophy (MSA), comprising the steps of
   a) adding alpha-synuclein as a native conformation prion protein to the sample to form a mixture and adding to the mixture at least one luminescent dye that is specific for the aggregated conformation prion protein and measuring the luminescence of the dye,
   b) subjecting the mixture comprising the sample and alpha-synuclein obtained in step a) to at least one shear-force intensity that is computer-controlled to have a uniform intensity having an intensity range of maximally 20% of one shear-force value for one or a plurality of cycles of shear-force acting and resting;
   c) following step b), determining via computer and storing the content of aggregated conformation prion protein for each of the shear-force intensities, and
   d) comparing, with a computer, the content of aggregated conformation prion protein determined in step c) to data in a computer-based databank on the content of aggregated conformation prion protein, which content was determined for alpha-synuclein as a native conformation prion protein subjected to the same shear-force intensity as in step b), wherein the data on the content of aggregated conformation prion protein was determined in alpha-synuclein as a native conformation prion protein in admixture with a reference sample and these data are provided in the computer-based databank which in association with these data contains the neurodegenerative prion-protein aggregation disease diagnosis of one or more of Idiopathic Parkinson's Disease (IPD), Parkinson's Disease with Dementia (PDD), Dementia with Lewy-Bodies (DLB) and Multiple System Atrophy (MSA) for the patient from which the reference sample originates.

2. The process according to claim 1, wherein prior to step b) the mixture is divided into aliquots and in step b) at least two aliquots are subjected to a different shear-force intensity each and in step c) the content of aggregated conformation prion protein is determined for each aliquot and in step d) the content of aggregated conformation prion protein determined in step c) for each aliquot is compared to data on a content of aggregated conformation prion protein.

3. The process according to claim 1, wherein in step b) the mixture is subjected to a succession of at least two different shear-force intensities and the content of aggregated conformation prion protein is determined during or following subjecting the mixture to each one of the shear-force intensities.

4. The process according to claim 1, comprising irradiating the mixture with light having a wavelength for exciting luminescence in the dye and measuring the luminescence of the dye during shear-force acting of step b) or during a resting phase of step b), without moving the volume occupied by the mixture relative a the shear-force generator generating the shear-force in step b).

5. The process according to claim 1, wherein in step b) the rate of formation of aggregated conformation prion protein is determined from the content of aggregated state prion protein determined at the at least one shear-force intensity and the data contain the rate of formation at the same shear-force intensity.

6. The process according to claim 1, wherein the content of aggregated conformation prion protein is determined as the time-resolved content and that the rate of formation of aggregated conformation prion protein is determined by non-linear regression analysis of an approximation on the determined time-resolved content of aggregated conformation prion protein for each of the shear-force intensities.

7. The process according to claim 1, characterized by adding at least one aggregated conformation prion protein to at least one aliquot of the mixture comprising the sample and alpha-synuclein as a native conformation prion protein, wherein the alpha-synuclein in aggregated conformation is produced by subjecting native alpha-synuclein as a native conformation prion protein to a uniform shear-force controlled to an intensity range of maximally 1% of one shear-force intensity.

8. A process for analysis for the presence of neurodegenerative prion-protein aggregation disease-related aggregated conformation prion protein in a biopsied mammalian sample, comprising the steps of
   a) adding alpha-synuclein as a native conformation prion protein to the sample to form a mixture;
   b) subjecting the mixture comprising the sample and alpha-synuclein as a native conformation prion protein obtained in step a) to at least one shear-force intensity that is computer-controlled to have a uniform intensity having an intensity range of maximally 20% of one shear-force value for one or a plurality of cycles of shear-force acting and resting;
   c) following step b), determining via computer and storing the content of aggregated conformation prion protein for each of the shear-force intensities, and
   d) comparing, with a computer, the content of aggregated conformation prion protein determined in step c) to data in a computer-based databank on the content of aggregated conformation prion protein, which content was determined for alpha-synuclein as a native conformation prion protein subjected to the same shear-force intensity as in step b), wherein the data on the content of aggregated conformation prion protein was determined in alpha-synuclein as a native conformation prion protein in admixture with a reference sample and these data are provided in the computer-based databank which in association with these data contains the neurodegenerative prion-protein aggregation disease diagnosis of one or more of Idiopathic Parkinson's Disease (IPD), Parkinson's Disease with Dementia (PDD), Dementia with Lewy-Bodies (DLB) and Multiple System Atrophy (MSA) for the patient from which the reference sample originates, the method further comprising irradiating the mixture with light having a wavelength that is scattered by the aggregated conformation prion protein and measuring scattered light exiting the admixture during step b), or during a pause of step b), with or without moving the volume occupied by the mixture relative a the shear-force generator generating the shear force in step b).

9. The process according to claim 8, comprising adding to the mixture at least one luminescent dye that is specific for the aggregated conformation prion protein prior to the step of subjecting the mixture to at least two different shear-force intensities and measuring the luminescence of the dye.

\* \* \* \* \*